United States Patent
Webber et al.

(10) Patent No.: US 11,191,841 B2
(45) Date of Patent: Dec. 7, 2021

(54) SUPRAMOLECULAR MODIFICATION OF PROTEINS

(71) Applicant: Massachusetts Institute of Technology, Cambridge, MA (US)

(72) Inventors: Matthew J. Webber, Cambridge, MA (US); Eric Andrew Appel, Palo Alto, CA (US); Robert S. Langer, Newton, MA (US); Daniel Griffith Anderson, Framingham, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 298 days.

(21) Appl. No.: 15/765,585

(22) PCT Filed: Oct. 6, 2016

(86) PCT No.: PCT/US2016/055755
§ 371 (c)(1),
(2) Date: Apr. 3, 2018

(87) PCT Pub. No.: WO2017/062622
PCT Pub. Date: Apr. 13, 2017

(65) Prior Publication Data
US 2018/0296680 A1  Oct. 18, 2018

Related U.S. Application Data

(60) Provisional application No. 62/334,910, filed on May 11, 2016, provisional application No. 62/237,836, filed on Oct. 6, 2015.

(51) Int. Cl.
| | |
|---|---|
| *A61K 47/60* | (2017.01) |
| *A61K 47/34* | (2017.01) |
| *C07K 14/62* | (2006.01) |
| *C07D 519/00* | (2006.01) |
| *C07K 14/605* | (2006.01) |
| *A61K 47/54* | (2017.01) |
| *A61K 47/68* | (2017.01) |
| *A61K 38/26* | (2006.01) |
| *A61K 38/28* | (2006.01) |
| *C07K 16/28* | (2006.01) |

(52) U.S. Cl.
CPC ............ *A61K 47/545* (2017.08); *A61K 38/26* (2013.01); *A61K 38/28* (2013.01); *A61K 47/34* (2013.01); *A61K 47/60* (2017.08); *A61K 47/6889* (2017.08); *C07D 519/00* (2013.01); *C07K 14/605* (2013.01); *C07K 14/62* (2013.01); *C07K 16/2896* (2013.01)

(58) Field of Classification Search
CPC .................................................. A61K 47/545
See application file for complete search history.

(56) References Cited

U.S. PATENT DOCUMENTS

| | | | | |
|---|---|---|---|---|
| 2006/0292570 | A1* | 12/2006 | Keinan | ............... C07D 487/22 435/6.16 |
| 2008/0279950 | A1 | 11/2008 | Kim et al. | |
| 2009/0068589 | A1 | 3/2009 | Fedynshyn | |

OTHER PUBLICATIONS

Ahn et al., Supramolecular velcro for reversible underwater adhesion. Angew Chem Int Ed Engl. Mar. 11, 2013;52(11):3140-4. doi: 10.1002/anie.201209382. Epub Feb. 4, 2013.
Bush et al., Charge-mediated recognition of N-terminal tryptophan in aqueous solution by a synthetic host. J Am Chem Soc. Oct. 19, 2005;127(41):14511-7.
Caliceti et al., Pharmacokinetic and biodistribution properties of poly(ethylene glycol)-protein conjugates. Adv Drug Deliv Rev. Sep. 26, 2003;55(10):1261-77.
Cao et al., Cucurbit[7]uril containers for targeted delivery of oxaliplatin to cancer cells. Angew Chem Int Ed Engl. Nov. 11, 2013;52(46):12033-7. doi: 10.1002/anie.201305061. Epub Sep. 13, 2013.
Chinai et al., Molecular recognition of insulin by a synthetic receptor. J Am Chem Soc. Jun. 15, 2011;133(23):8810-3. doi: 10.1021/ja201581x. Epub Apr. 7, 2011.
Chou et al., Glucose-responsive insulin activity by covalent modification with aliphatic phenylboronic acid conjugates. Proc Natl Acad Sci USA. Feb. 24, 2015;112(8):2401-6. doi: 10.1073/pnas. 1424684112. Epub Feb. 9, 2015.
Davis et al., Cyclodextrin-based pharmaceutics: past, present and future. Nat Rev Drug Discov. Dec. 2004;3(12):1023-35. doi: 10.1038/ nrd1576.
Del Valle, Cyclodextrins and their uses: a review. Process Biochem. May 31, 2004;39(9):1033-1176.
Dutta Choudhury et al., Photophysical studies on the noncovalent interaction of thioflavin T with cucurbit[n]uril macrocycles. J Phys Chem B. Feb. 19, 2009;113(7):1891-8. doi: 10.1021/jp8103062.
Harris et al., Effect of pegylation on pharmaceuticals. Nat Rev Drug Discov. Mar. 2003;2(3):214-21.

(Continued)

*Primary Examiner* — Yong S. Chong
(74) *Attorney, Agent, or Firm* — Wolf, Greenfield & Sacks, P.C.

(57) ABSTRACT

The modification of biomolecules, small molecules, and other agents of via conjugation of excipients, tags, or labels is of great importance. For example, the modification of therapeutic agents can confer improved stability, solubility, duration of action, or pharmacological properties. Supramolecular chemistry utilizes specific, directional, reversible, non-covalent molecular recognition motifs in order to achieve organization of molecules, and can be used to complex tags to agents of interest (e.g., insulin, glucagon, antibodies). The present invention provides useful supramolecular complexes wherein an agent of interest is specifically bound to a host via non-covalent interactions, and wherein the host is conjugated to a tag. The present invention also provides methods and compounds useful in preparing supramolecular complexes, and methods of treating diseases using the supramolecular complexes.

30 Claims, 12 Drawing Sheets

(56) References Cited

OTHER PUBLICATIONS

Heitmann et al., Sequence-specific recognition and cooperative dimerization of N-terminal aromatic peptides in aqueous solution by a synthetic host. J Am Chem Soc. Sep. 27, 2006;128(38):12574-81.
Hinds et al., Synthesis and characterization of poly(ethylene glycol)-insulin conjugates. Bioconjug Chem. Mar.-Apr. 2000;11(2):195-201.
Hinds et al., Effects of PEG conjugation on insulin properties. Adv Drug Deliv Rev. Jun. 17, 2002;54(4):505-30.
Hirsch, Insulin analogues. N Engl J Med. Jan. 13, 2005;352(2):174-83.
Jevsevar et al., PEGylation of therapeutic proteins. Biotechnol J. Jan. 2010;5(1):113-28. doi: 10.1002/biot.200900218.
Kamerzell et al., Protein-excipient interactions: mechanisms and biophysical characterization applied to protein formulation development. Adv Drug Deliv Rev. Oct. 2011;63(13):1118-59. doi: 10.1016/j.addr.2011.07.006. Epub Jul. 29, 2011.
Keefe et al., Poly(zwitterionic)protein conjugates offer increased stability without sacrificing binding affinity or bioactivity. Nat Chem. Jan. 2012;4(1):59-63. doi: 10.1038/nchem.1213.
Kim et al., Functionalized cucurbiturils and their applications. Chem Soc Rev. Feb. 2007;36(2):267-79. Epub Nov. 7, 2006.
Lee et al., Supramolecular inhibition of amyloid fibrillation by cucurbit[7]uril. Angew Chem Int Ed Engl. Jul. 14, 2014;53(29):7461-5. doi: 10.1002/anie.201402496. Epub May 19, 2014.
Lee et al., Cucurbituril homologues and derivatives: new opportunities in supramolecular chemistry. Acc Chem Res. Aug. 2003;36(8):621-30.
Lehn et al., Supramolecular Chemistry—Scope and Perspectives Molecules, Supermolecules, and Molecular Devices (Nobel Lecture). Angewandte Chemie International Edition in English. Jan. 1988;27(1):89-112. doi: 10.1002/anie.198800891.
Lehn, Toward complex matter: supramolecular chemistry and self-organization. Proc Natl Acad Sci USA. Apr. 16, 2002;99(8):4763-8. Epub Apr. 2, 2002.
Liu et al., The cucurbit[n]uril family: prime components for self-sorting systems. J Am Chem Soc. Nov. 16, 2005;127(45):15959-67.
Logsdon et al., Nanomolar binding of peptides containing noncanonical amino acids by a synthetic receptor. J Am Chem Soc. Oct. 26, 2011;133(42):17087-92. doi: 10.1021/ja207825y. Epub Oct. 3, 2011.
Lougheed et al., Insulin aggregation in artificial delivery systems. Diabetologia. Jul. 1980;19(1):1-9.
Ma et al., Acyclic cucurbit[n]uril molecular containers enhance the solubility and bioactivity of poorly soluble pharmaceuticals. Nat Chem. Apr. 15, 2012;4(6):503-10. doi: 10.1038/nchem.1326.
Rekharsky et al., A synthetic host-guest system achieves avidin-biotin affinity by overcoming enthalpy-entropy compensation. Proc Natl Acad Sci USA. Dec. 26, 2007;104(52):20737-42. Epub Dec. 19, 2007.
Roberts et al., Chemistry for peptide and protein PEGylation. Adv Drug Deliv Rev. Jun. 17, 2002;54(4):459-76.
Schneider, Mechanisms of Molecular Recognition : Investigations of Organic Host-Guest Complexes. Angew Chem Int Edit. Nov. 1991; 30(11):1417-1436. doi: 10.1002/anie.199114171.
Uekama et al., Cyclodextrins in drug carrier systems. Crit Rev Ther Drug Carrier Syst. 1987;3(1):1-40.
Veronese, Peptide and protein PEGylation: a review of problems and solutions. Biomaterials. Mar. 2001;22(5):405-17.
Veronese et al., PEGylation, successful approach to drug delivery. Drug Discov Today. Nov. 1, 2005;10(21):1451-8.
Vinciguerra et al., Synthesis and self-assembly processes of monofunctionalized cucurbit[7]uril. J Am Chem Soc. Aug. 8, 2012;134(31):13133-40. doi: 10.1021/ja3058502. Epub Jul. 30, 2012.
International Preliminary Report on Patentability for PCT/US2016/055755, dated Apr. 19, 2018.
International Search Report and Written Opinion for PCT/US2016/055755, dated Feb. 16, 2017.
Barrow et al., Cucurbituril-Based Molecular Recognition. Chem Rev. Nov. 25, 2015;115(22):12320-406. doi: 10.1021/acs.chemrev.5b00341. Epub Nov. 13, 2015. Erratum in: Chem Rev. Oct. 12, 2016;116(19):12651-12652. PMID: 26566008.
Urbach et al., Molecular Recognition of Amino Acids, Peptides, and Proteins by Cucurbit[n]uril Receptors. Israel Journal of Chemistry. May 2011;51(5-6):664-678.
PCT/US2016/055755, Apr. 19, 2018, International Preliminary Report on Patentability.
PCT/US2016/055755, Feb. 16, 2017, International Search Report and Written Opinion.

* cited by examiner

SUPRAMOLECULAR MODIFICATION OF PROTEINS

RELATED APPLICATIONS

This application is a national stage filing under 35 U.S.C. § 371 of international PCT application, PCT/US2016/055755, filed Oct. 6, 2016, which claims priority under 35 U.S.C. § 119(e) to U.S. provisional patent applications, U.S. Ser. No. 62/237,836, filed Oct. 6, 2015, and U.S. Ser. No. 62/334,910, filed May 11, 2016, each of which is incorporated herein by reference.

GOVERNMENT SUPPORT

This invention was made with Government support under Grant No. R37 EB000244 awarded by the National Institutes of Health. The Government has certain rights in the invention.

BACKGROUND OF THE INVENTION

The practice of medicine has been transformed by the use of biopharmaceuticals, with many drugs coming to market in recent years in the form of peptides and proteins (e.g., insulin, antibodies, cytokines). See, e.g., Carter P J. *Nat Rev Immunol* 2006, 6(5): 343-357; Aggarwal R S. *Nat Biotechnol* 2014, 32(1): 32-39. These new classes of drugs have an array of attendant complications that arise from poor chemical and/or structural stability that can lead to the active drug being converted into an inactive and/or potentially immunogenic form. See, e.g., Shire et al. *J Pharm Sci* 2004, 93(6): 1390-1402; Hermeling et al. *Pharmaceutical research* 2004, 21(6): 897-903. Extensive efforts have been devoted to the development of excipients for use in the formulation of biomolecules (e.g., proteins, antibodies) to confer improved stability. See, e.g., Wang et al. *Int J Pharm* 1999, 185(2): 129-188. For example, excipients commonly used in the formulation of biomolecules include salts, sugars, amino acids, non-ionic surfactants, chelators, anti-microbial preservatives, carrier proteins, and polymers. See, e.g., Kamerzell et al. *Adv Drug Deliv Rev* 2011, 63(13): 1118-1159. The mechanisms by which these excipients act are varied and can include direct interaction with the protein via electrostatic, cation-π, or hydrogen bonding interactions, preferential protein hydration, enhancement of dispersive forces, cryo-stabilization during lyophilization, coating of exposed hydrophobic patches on protein surfaces, or coating of air-liquid and solid-liquid interfaces to prevent nucleation of protein unfolding and aggregation. An alternate approach to promote stability or modify pharmacological activity of drugs or other agents is through direct covalent modification. One of the most common modification strategies has been covalent attachment of poly(ethylene glycol) (PEG), which is intended to increase protein solubility, limit exposure to proteolytic enzymes or opsonins, increase the effective hydrodynamic size of the protein to reduce glomerular filtration, and/or inhibit protein aggregation. See, e.g., Veronese F M. *Biomaterials* 2001, 22(5): 405-417; Roberts et al. *Adv Drug Deliv Rev* 2002, 54(4): 459-476; Harris et al. *Nat Rev Drug Discov* 2003, 2(3): 214-221; Jevsevar et al. *Biotechnology Journal* 2010, 5(1): 113-128; Veronese et al. *Drug Discov Today* 2005, 10(21): 1451-1458. An alternative approach has relied on direct conjugation of zwitterionic polymers to fulfill similar objectives. See, e.g., Keefe et al. *Nature Chemistry* 2012, 4(1): 59-63. PEGylated biopharmaceuticals have been used clinically for a range of diseases, for example, with interferon treatment of hepatitis B, hepatitis C, and multiple sclerosis. An important issue with direct conjugation is ensuring site-specific modification away from the active site of the therapeutic in order to limit deleterious effects of the modification on protein function.

Supramolecular chemistry, defined as "chemistry beyond the molecule," utilizes specific, directional, reversible, non-covalent molecular recognition motifs in order to achieve organization of molecules. See, e.g., Lehn et al. *Angewandte Chemie International Edition in English* 1988, 27(1): 89-112; Lehn et al. *Proc Natl Acad Sci USA* 2002, 99(8): 4763-4768; Supramolecular host-guest motifs typically comprise a discrete macrocyclic host with a cavity that is selective for complimentary binding to certain guest ligands. See, e.g., Schneider et al. *Angew Chem Int Edit* 1991, 30(11): 1417-1436. In aqueous environments, several families of cyclic hosts, including cyclodextrins and cucurbiturils, select for inclusion of hydrophobic guests within their cavity. See, e.g., Liu et al. *Journal of the American Chemical Society* 2005, 127(45): 15959-15967; Del Valle et al. *Process Biochem* 2004, 39(9): 1033-1046; Biedermann et al. *Journal of the American Chemical Society* 2012, 134(37): 15318-15323. The affinity of a number of hydrophobic small molecule drugs with these hosts has been leveraged as a strategy to solubilize a wide variety of pharmaceutical compounds. See, e.g., Davis et al. *Nat Rev Drug Discov* 2004, 3(12): 1023-1035; Uekama et al. *Crit Rev Ther Drug* 1987, 3(1): 1-40. Cucurbit[7]uril (CB[7]) has also been demonstrated to bind proteins with N-terminal aromatic amino acids (e.g., tryptophan and phenylalanine) through a combination of R-group inclusion within the cavity and electrostatic interactions between the protonated N-terminal amine and the carbonyl functionality on the CB[7] portal. For example, CB[7] can bind to insulin via its B1 phenylalanine residue. See, e.g., Bush et al. *Journal of the American Chemical Society* 2005, 127(41): 14511-14517; Heitmann et al. *Journal of the American Chemical Society* 2006, 128(38): 12574-12581; Chinai et al. *Journal of the American Chemical Society* 2011, 133(23): 8810-8813.

New strategies for the modification and formulation of compounds are needed, and supramolecular guest-host chemistry has great utility in this regard. In particular, supramolecular conjugates of therapeutic agents can help achieve improved stability and duration of action of the therapeutic agent.

SUMMARY OF THE INVENTION

Alternative means of modifying biomolecules that do not rely on covalent bonding are desired; in particular, site-specific non-covalent complexation is an attractive option. Moreover, this concept can be extended beyond biomolecules to aid in the modification of small molecules, diagnostic agents, imaging agents, etc. Supramolecular chemistry utilizes specific, directional, reversible, non-covalent molecular recognition motifs in order to achieve organization of molecules. In particular, supramolecular chemistry can be used to bind agents, such as biomolecules (e.g., peptides, proteins, nucleic acids), small molecule drugs, and imaging agents, and diagnostic agents to excipients and other tags. The present invention provides useful supramolecular complexes comprising an agent associated with a tag, wherein the agent is specifically bound to a host via non-covalent guest-host interactions, and wherein the host is conjugated to the tag. The present invention also provides methods and compounds useful in preparing the supramolecular complexes described herein, methods of treating diseases using the supramolecular complexes, as well as compositions and kits comprising the supramolecular complexes.

In one aspect, the present invention provides an agent associated with a tag (also referred to herein as a "supramolecular complex"), wherein the agent is specifically bound to a host via non-covalent guest-host interactions, and wherein the host is conjugated to the tag. In certain embodiments of the invention, the agent that is associated with a tag is a biomolecule (e.g., peptide, protein, nucleic acid), small molecule drug, excipient, diagnostic agent, imaging agent, etc. In some embodiments, the host is a macrocyclic host, such as a cucurbituril, cyclodextrin, calixarene, pillararene, porphyrin, metallacrown, crown ether, cyclotriveratrylene, cryptophane, or carcerand. Examples of tags that are associated with the agent include excipients, labels, therapeutic agents, diagnostic agents, etc.

In another aspect, the present invention describes methods for preparing supramolecular complexes comprising an agent associated with a tag. In some embodiments, these methods comprise contacting an agent with a host conjugated to a tag (also referred to herein as a "host-tag conjugate").

In another aspect, the present invention provides a host conjugated to a tag ("host-tag conjugate"). These compounds are useful in the preparation of the supramolecular complexes described herein. In some embodiments, the host is a macrocyclic host. In some embodiments, the host conjugated to a tag is a cucurbituril; and the tag is optionally selected from the group consisting of polymers, targeting agents, radionuclides, fluorophores, chromophores, phosphorescent agents, dyes, chemiluminescent agents, particles, colorimetric labels, magnetic labels, haptens, biomolecules, fatty acids, hydrocarbon chains, excipients, and small molecules. In certain embodiments, the tag is another biomolecule, such as a peptide, protein (e.g., antibody), nucleic acid, etc.

In another aspect, the present invention describes methods for preparing the host-tag conjugates described herein. In certain embodiments of the invention, these compounds can be prepared by linking a host molecule to a tag using covalent bond-forming reactions. For example, in some embodiments, "click chemistry" is used to conjugate the host to the tag.

In another aspect, the present invention provides pharmaceutical compositions including a supramolecular complex described herein, and optionally a pharmaceutically acceptable excipient. In certain embodiments, the pharmaceutical composition comprises an effective amount (e.g., therapeutically or prophyllatically effective amount) of the supramolecular complex).

The present invention also provides methods for treating diseases in a subject in need thereof by administering to a subject in need thereof an effective amount of a supramolecular complex described herein, or a pharmaceutical composition thereof. In addition, the present invention provides uses of the supramolecular complexes provided herein for the treatment of diseases described herein. The present invention also provides uses of the supramolecular complexes provided herein for the preparation of medicaments (i.e., medicaments for the treatment of diseases described herein). Further, the present invention provides supramolecular complexes, and pharmaceutical compositions thereof, for use in the treatment of diseases described herein.

In another aspect, the present disclosure relates to kits comprising a supramolecular complex described herein, or pharmaceutical composition thereof, as described herein.

The kits may be useful in a method of the disclosure. In certain embodiments, the kit further includes instructions for using the complex or pharmaceutical composition. In yet another aspect, the present invention relates to kits comprising compounds that are useful in the preparation of supramolecular complexes or intermediates thereto as described herein.

The details of certain embodiments of the invention are set forth in the Detailed Description of Certain Embodiments. Other features, objects, and advantages of the invention will be apparent from the Definitions, Examples, Figures, and Claims.

BRIEF DESCRIPTION OF THE DRAWINGS

The accompanying drawings, which are incorporated in and constitute a part of this specification, illustrate several embodiments of the invention and together with the description, serve to explain the principles of the invention.

(FIG. 1A) A copper free "click" reaction between a cucurbit[7]uril (CB[7]) supramolecular host molecule bearing a single azide moiety and a dibenzocyclooctyne-functionalized poly(ethylene glycol) polymer (PEG-DBCO; $M_n$=5 kDa, 10 kDa, or 30 kDa) yields PEG-T-CB[7] conjugate upon triazole formation (n. b. only one of two possible regioisomers for triazole formation is shown). (FIG. 1B) Schematic representation of supramolecular PEGylation of native insulin with PEG-T-CB [7] via strong non-covalent binding of the CB [7] moiety to the B1 phenylalanine residue.

(FIG. 2A) UV-visible absorbance of $PEG_{30k}$-DBCO and $PEG_{30k}$-T-CB[7] indicates a change in the $\lambda_{max}$ of the DBCO moiety upon conjugation of the CB[7]-$N_3$ and corresponding formation of a triazole. (FIG. 2B) Overlay of refractive index and absorbance (triazole $\lambda_{max}$=245 nm) traces from gel permeation chromatography demonstrates co-elution of the triazole and the polymeric species. (FIG. 2C) MALDI-MS characterization indicates an increase in mass of the PEG species corresponding to conjugation of the CB[7] moiety. (FIG. 2D) Acridine orange (AO) competitive binding assay with native insulin indicates no significant alteration of the CB[7]-Insulin binding occurs following PEG conjugation (CB[7], $K_D$=2.3±0.2 µM; $PEG_{5k}$-T-CB[7], $K_D$=1.4±0.1 µM; $PEG_{10k}$-T-CB[7], $K_D$=1.3±0.1 µM; $PEG_{30k}$-T-CB[7], $K_D$=2.1±0.3 µM), using AO (8 µM), CB[7] or PEG-T-CB[7] (6 µM), and insulin (varied from 0-15 µM), with binding studies performed in water. The intensity at 510 nm was used in fitting the decay of signal.

(FIG. 3A) Kinetic studies of the aggregation of various insulin formulations at pH 7.4, 37° C., in physiological buffer with continuous agitation over the course of 100 hours. (FIG. 3B) Quantification of the aggregation time of various insulin formulations (where $CB[7]_{5k}$ denotes addition of $PEG_{5k}$-T-CB[7]). Rapid aggregation of native insulin with and without CB[7] is observed, while supramolecular PEGylation of insulin with PEG-T-CB[7] promotes dramatically increased stability under these conditions. At the 50-day endpoint of the study, none of the PEG-T-CB[7] formulations had aggregated.

(FIG. 9) Anti-CD20 antibody, aged in formulation with CB[7] or CB[7]-PEG was evaluated for reactivity against $CD20^+$ Raji cells, analyzed by flow cytometry after incubation with cells and subsequent labeling with a fluorescent anti-IgG secondary antibody. Median fluorescent intensity (MFI) is shown for each group. Antibody reactivity of Raji cells is preserved only in the case where antibody is aged in the presence of CB[7]-PEG. (FIG. 9B) Glucagon, when formulated with CB[7]-$PEG_{10k}$, remains soluble for at least 24 hours, whereas it readily precipitates from solution when dissolved alone. (FIG. 9C) Near ultraviolet circular dichroism demonstrates glucagon aged for 24 hours in the presence of CB[7]-$PEG_{10k}$ remains in an active α-helix conformation, and there is no appreciable glucagon in solution when aged.

DEFINITIONS

Chemical Definitions

Figure 1A:
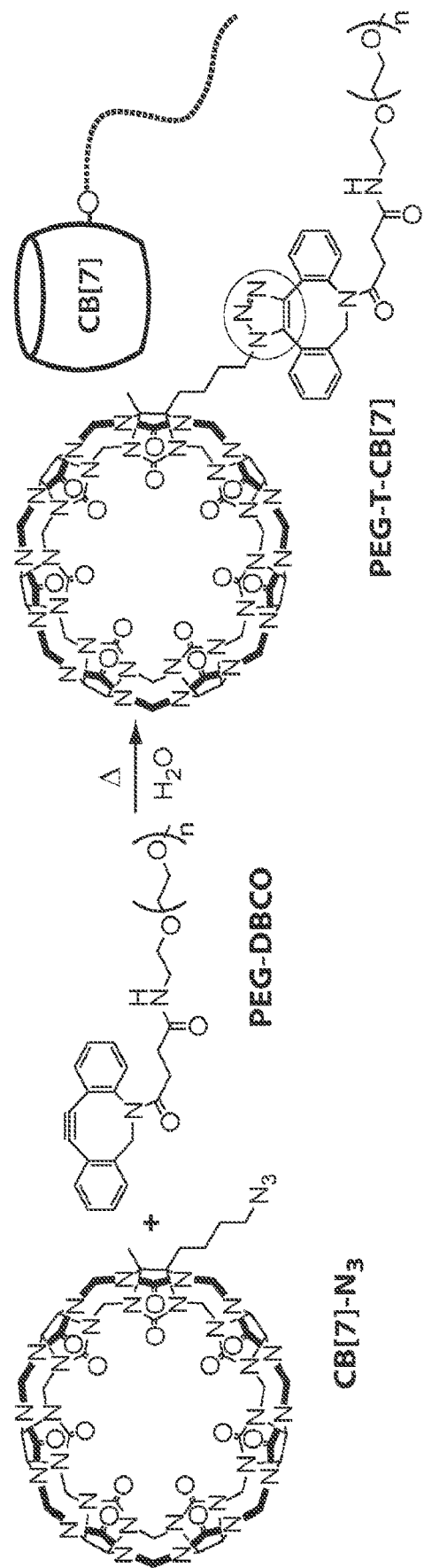
FIGS. 1A-1B. Supramolecular PEGylation of native insulin.
Figure 1B:
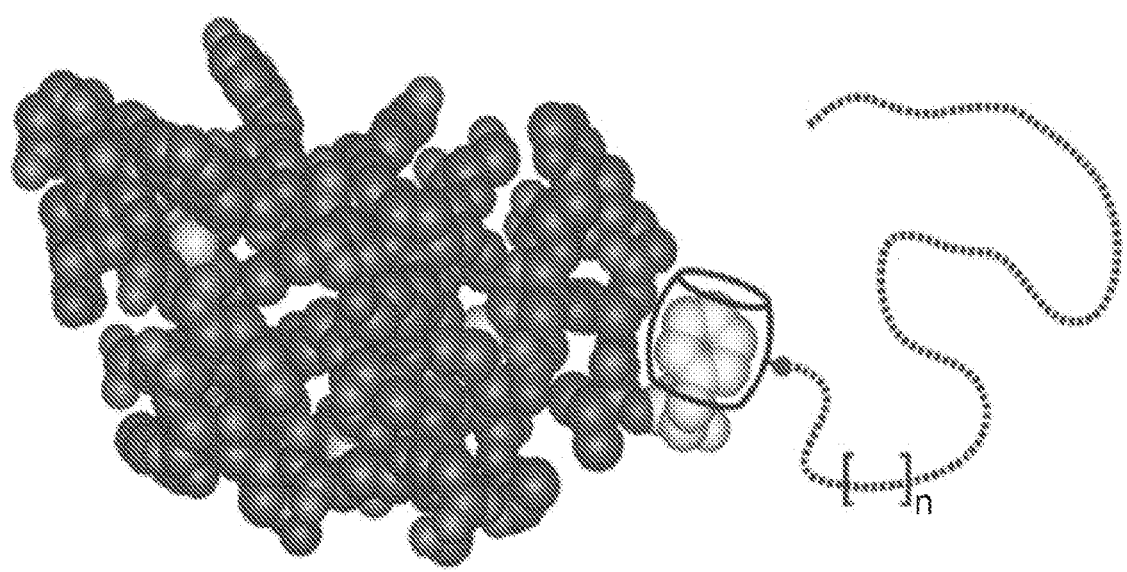

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of *organic chemistry*, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl($C_1$), ethyl($C_2$), propyl($C_3$) (e.g., n-propyl, isopropyl), butyl($C_4$) (e.g., n-butyl, tert-butyl, sec-butyl, iso-butyl), pentyl($C_5$) (e.g., n-pentyl, 3-pentanyl, amyl, neopentyl, 3-methyl-2-butanyl, tertiary amyl), and hexyl($C_6$) (e.g., n-hexyl). Additional examples of alkyl groups include n-heptyl($C_7$), n-octyl($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl(Et), unsubstituted propyl(Pr, e.g., unsubstituted n-propyl(n-Pr), unsubstituted isopropyl(i-Pr)), unsubstituted butyl (Bu, e.g., unsubstituted n-butyl(n-Bu), unsubstituted tert-butyl(tert-Bu or t-Bu), unsubstituted sec-butyl(sec-Bu), unsubstituted isobutyl(i-Bu)). In certain embodiments, the alkyl group is a substituted $C_{1-10}$ alkyl (such as substituted $C_{1-6}$ alkyl, e.g., —CF$_3$, Bn).

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

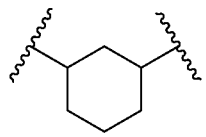 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

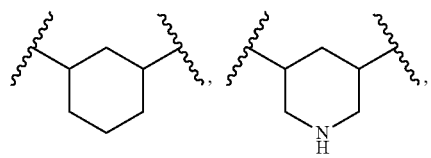

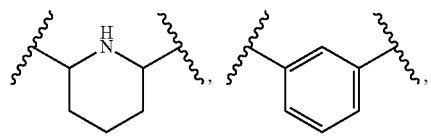

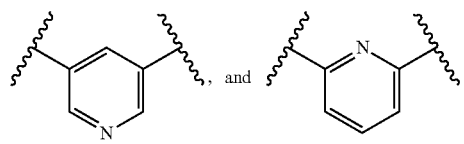

are all examples of a hydrocarbon chain. In contrast, in certain embodiments,

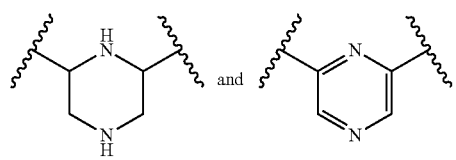 [SMILES: *C1CNCC(*)N1 ; *c1cncc(*)n1]

are not within the scope of the hydrocarbon chains described herein. When a chain atom of a C$_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

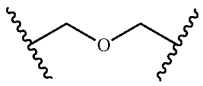 [SMILES: *COC*]

is a $C_3$ hydrocarbon chain wherein one chain atom is replaced with an oxygen atom.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl($C_2$), 1-propenyl($C_3$), 2-propenyl($C_3$), 1-butenyl($C_4$), 2-butenyl($C_4$), butadienyl ($C_4$), and the like. Examples of $C_{2-6}$ alkenyl groups include the aforementioned $C_{2-4}$ alkenyl groups as well as pentenyl ($C_5$), pentadienyl($C_5$), hexenyl($C_6$), and the like. Additional examples of alkenyl include heptenyl($C_7$), octenyl($C_8$), octatrienyl($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl($C_2$), 1-propynyl($C_3$), 2-propynyl($C_3$), 1-butynyl ($C_4$), 2-butynyl($C_4$), and the like. Examples of $C_{2-6}$ alkenyl groups include the aforementioned $C_{2-4}$ alkynyl groups as well as pentynyl($C_5$), hexynyl($C_6$), and the like. Additional examples of alkynyl include heptynyl($C_7$), octynyl($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl(C$_3$), cyclopropenyl(C$_3$), cyclobutyl(C$_4$), cyclobutenyl(C$_4$), cyclopentyl(C$_5$), cyclopentenyl(C$_5$), cyclohexyl(C$_6$), cyclohexenyl(C$_6$), cyclohexadienyl(C$_6$), and the like. Exemplary C$_{3-8}$ carbocyclyl groups include, without limitation, the aforementioned C$_{3-6}$ carbocyclyl groups as well as cycloheptyl(C$_7$), cycloheptenyl(C$_7$), cycloheptadienyl(C$_7$), cycloheptatrienyl(C$_7$), cyclooctyl(C$_8$), cyclooctenyl(C$_8$), bicyclo[2.2.1]heptanyl (C$_7$), bicyclo[2.2.2]octanyl(C$_8$), and the like. Exemplary C$_{3-10}$ carbocyclyl groups include, without limitation, the aforementioned C$_{3-8}$ carbocyclyl groups as well as cyclononyl(C$_9$), cyclononenyl(C$_9$), cyclodecyl(C$_{10}$), cyclodecenyl(C$_{10}$), octahydro-1H-indenyl(C$_9$), decahydronaphthalenyl(C$_{10}$), spiro[4.5]decanyl(C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl(C$_5$) and cyclohexyl(C$_5$). Examples of C$_{3-6}$ cycloalkyl groups include the aforementioned C$_{5-6}$ cycloalkyl groups as well as cyclopropyl(C$_3$) and cyclobutyl(C$_4$). Examples of C$_{3-8}$ cycloalkyl groups include the aforementioned C$_{3-6}$ cycloalkyl groups as well as cycloheptyl(C$_7$) and cyclooctyl(C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, aziridinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 t electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^−$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+X^−$, —N(O$R^{ee}$)$R^{ff}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2R^{ee}$, —SO$_2$N($R^{ff}$)$_2$, —SO$_2R^{ee}$, —SO$_2$O$R^{ee}$, —OSO$_2R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^−$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^−$, —NH($C_{1-6}$ alkyl)$_2^+X^−$, —NH$_2$($C_{1-6}$ alkyl)$^+X^−$, —NH$_3^+X^−$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2C_{1-6}$ alkyl, —SO$_2$O$C_{1-6}$ alkyl, —OSO$_2C_{1-6}$ alkyl, —SO$C_{1-6}$ alkyl, —Si($C_{1-6}$ alkyl)$_3$, —OSi($C_{1-6}$ alkyl)$_3$ -C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S) S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^−$ is a counterion.

The term "halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N ($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$) O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl] methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR$^{cc}$)$_3$$^+$X$^-$, —P(=O) (R$^{aa}$)$_2$, —P(=O)(OR$^{cc}$)$_2$, and —P(=O)(N(R$^{bb}$)$_2$)$_2$, wherein X⁻, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl(p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl(Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F⁻, Cl⁻, Br⁻, I⁻), $NO_3^-$, $ClO_4^-$, OH⁻, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F⁻, Cl⁻, Br⁻, I⁻), $NO_3^-$, $ClO_4^-$, OH⁻, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5\text{-}(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The "molecular weight" of a monovalent moiety —R is calculated by subtracting 1 from the molecular weight of the compound R—H. The "molecular weight" of a divalent moiety -L- is calculated by subtracting 2 from the molecular weight of the compound H-L-H.

The term "lipophilic" or "hydrophobic" refers to the ability of a compound to dissolve, or the ability of a moiety of a compound to assist the compound in dissolving in fats, oils, lipids, and/or non-polar solvents (e.g., hexane or toluene). Lipophilic moieties include, but are not limited to, substituted or unsubstituted, branched or unbranched alkyl groups having 1 to 50 carbon atoms. In certain embodiments, the lipophilic moiety is an alkyl group including at least 1, at least 6, at least 12, at least 18, at least 24, at least 36, or at least 50 carbon atoms. In certain embodiments, the lipophilic moiety is an alkyl group including at most 50, at most 36, at most 24, at most 18, at most 12, or at most 6 carbon atoms. Combinations of the above-referenced ranges (e.g., at least about 1 and at most about 24 carbon atoms) are also within the scope of the invention. In certain embodiments, the lipophilic moiety is unsubstituted alkyl. In certain embodiments, the lipophilic moiety is unsubstituted and unbranched alkyl. In certain embodiments, the lipophilic moiety is unsubstituted and unbranched $C_{1-24}$ alkyl. In certain embodiments, the lipophilic moiety is unsubstituted and unbranched $C_{6-24}$ alkyl. In certain embodiments, the lipophilic moiety is unsubstituted and unbranched $C_{12-24}$ alkyl.

Other Definitions

The following definitions are more general terms used throughout the present application.

As generally defined herein, "biomolecule" refers to any compound or biological material which may be found in a living organism. Examples of classes of biomolecules include, but are not limited to, proteins, peptides, nucleic acids, lipids, polysaccharides, small molecules, primary metabolites, secondary metabolites, natural products, etc.

As used herein, the term "polymer" refers to any substance comprising at least two repeating structural units (i.e., "monomers") which are associated with one another. In some embodiments, monomers are covalently associated with one another. In some embodiments, monomers are non-covalently associated with one another. Polymers may be homopolymers or copolymers comprising two or more monomers. In terms of sequence, copolymers may be random, block, graft, or comprise a combination of random, block, and/or graft sequences. In some embodiments, block copolymers are diblock copolymers. In some embodiments, block copolymers are triblock copolymers. In some embodiments, polymers can be linear or branched polymers. In some embodiments, polymers in accordance with the invention comprise blends, mixtures, and/or adducts of any of the polymers described herein. Typically, polymers in accordance with the present invention are organic polymers. In some embodiments, polymers are hydrophilic. In some embodiments, polymers are hydrophobic. In some embodiments, polymers modified with one or more moieties and/or functional groups.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical agent such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these. A "native" or "wild type" protein or peptide refers to the protein or peptide as it is found in nature (i.e., without further modification). In certain embodiments, a protein useful in the present invention is a therapeutic protein. Examples of therapeutic proteins are provided below and elsewhere herein.

As generally defined herein, "therapeutic protein" refers to any protein or protein-based therapy that may be administered to a subject and have a therapeutic effect. Such therapies include protein replacement and protein supplementation therapies. Such therapies also include the administration of exogenous or foreign protein, antibody therapies, and cell or cell-based therapies. Therapeutic proteins include infusible therapeutic proteins, enzymes, enzyme cofactors, hormones, blood clotting factors, cytokines, growth factors, monoclonal antibodies, and polyclonal antibodies.

Examples of enzymes contemplated in the present invention include, but are not limited to, oxidoreductases, transferases, hydrolases, lyases, isomerases, and ligases.

Examples of hormones contemplated in the present invention include, but are not limited to, Melatonin (N-acetyl-5-methoxytryptamine), Serotonin, Thyroxine (or tetraiodothyronine) (a thyroid hormone), Triiodothyronine (a thyroid hormone), Epinephrine (or adrenaline), Norepinephrine (or noradrenaline), Dopamine (or prolactin inhibiting hormone), Antimullerian hormone (or mullerian inhibiting factor or hormone), adipokines (e.g., Leptin and Adiponectin), Adrenocorticotropic hormone (or corticotropin), Angiotensinogen and angiotensin, Antidiuretic hormone (or vasopressin, arginine vasopressin), Atrial-natriuretic peptide (or atriopeptin), Calcitonin, Cholecystokinin, Corticotropin-releasing hormone, Erythropoietin, Follicle-stimulating hormone, Gastrin, Ghrelin, Glucagon, Glucagon-like peptide (GLP-1), GIP, Gonadotropin-releasing hormone, Growth hormone-releasing hormone, Human chorionic gonadotropin, Human placental lactogen, Growth hormone, Inhibin, Insulin, Insulin-like growth factor (or somatomedin), Luteinizing hormone, Melanocyte stimulating hormone, Orexin, Oxytocin, Parathyroid hormone, Prolactin, Relaxin, Secretin, Somatostatin, Thrombopoietin, Thyroid-stimulating hormone (or thyrotropin), Thyrotropin-releasing hormone, Cortisol, Aldosterone, Testosterone, Dehydroepiandrosterone, Androstenedione, Dihydrotestosterone, Estradiol, Estrone, Estriol, Progesterone, Calcitriol (1,25-dihydroxyvitamin D3), Calcidiol (25-hydroxyvitamin D3), Prostaglandins, Leukotrienes, Prostacyclin, Thromboxane, Prolactin releasing hormone, Lipotropin, Brain natriuretic peptide, Neuropeptide Y, Histamine, Endothelin, Pancreatic polypeptide, Renin, and Enkephalin.

Examples of blood and blood coagulation factors contemplated in the present invention include, but are not limited to, Factor I (fibrinogen), Factor II (prothrombin), tissue factor, Factor V (proaccelerin, labile factor), Factor VII (stable factor, proconvertin), Factor VIII (antihemophilic globulin), Factor IX(Christmas factor or plasma thromboplastin component), Factor X(Stuart-Prower factor), Factor Xa, Factor XI, Factor XII(Hageman factor), Factor XIII (fibrin-stabilizing factor), von Willebrand factor, prekallikrein (Fletcher factor), high-molecular weight kininogen (HMWK) (Fitzgerald factor), fibronectin, fibrin, thrombin, antithrombin, antithrombin III, heparin cofactor II, protein C, protein S, protein Z, protein Z-related protease inhibitot (ZPI), plasminogen, alpha 2-antiplasmin, tissue plasminogen activator (tPA), urokinase, plasminogen activator inhibitor-1 (PAI1), von Heldebrant factor, plasminogen activator inhibitor-2 (PAI2), cancer procoagulant, and epoetin alfa (Epogen, Procrit).

Examples of cytokines include lymphokines, interleukins, and chemokines, type 1 cytokines, such as IFN-γ, TGF-β, and type 2 cytokines, such as IL-4, IL-10, and IL-13.

Examples of growth factors include Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha(TGF-α), Transforming growth factor beta(TGF-β), Tumour_necrosis_factor-alpha(TNF-α), Vascular endothelial growth factor (VEGF), Wnt Signaling Pathway, placental growth factor (PlGF), [(Foetal Bovine Somatotrophin)] (FBS), IL-1, IL-2, IL-3, IL-4, IL-5, IL-6, and IL-7.

Examples of monoclonal antibodies contemplated in the present invention include, but are not limited to, Abagovomab, Abciximab, Adalimumab, Adecatumumab, Afelimomab, Afutuzumab, Alacizumab pegol, ALD, Alemtuzumab, Altumomab pentetate, Anatumomab mafenatox, Anrukinzumab, Anti-thymocyte globin, Apolizumab, Arcitumomab, Aselizumab, Atlizumab (tocilizumab), Atorolimumab, Bapineuzumab, Basiliximab, Bavituximab, Bectumomab, Belimumab, Benralizumab, Bertilimumab, Besilesomab, Bevacizumab, Biciromab, Bivatuzumab mertansine, Blinatumomab, Brentuximab vedotin, Briakinumab, Canakinumab, Cantuzumab mertansine, Capromab pendetide, Catumaxomab, Cedelizumab, Certolizumab pegol, Cetuximab, Citatuzumab bogatox, Cixutumumab, Clenoliximab, Clivatuzumab tetraxetan, Conatumumab, Dacetuzumab, Daclizumab, Daratumumab, Denosumab, Detumomab, Dorlimomab aritox, Dorlixizumab, Ecromeximab, Eculizumab, Edobacomab, Edrecolomab, Efalizumab, Efungumab, Elotuzumab, Elsilimomab, Enlimomab pegol, Epitumomab cituxetan, Epratuzumab, Erlizumab, Ertumaxomab, Etaracizumab, Exbivirumab, Fanolesomab, Faralimomab, Farletuzumab, Felvizumab, Fezakinumab, Figitumumab, Fontolizumab, Foravirumab, Fresolimumab, Galiximab, Gantenerumab, Gavilimomab, Gemtuzumab ozogamicin, GC1008, Girentuximab, Glembatumumab vedotin, Golimumab, Gomiliximab, Ibalizumab, Ibritumomab tiuxetan, Igovomab, Imciromab, Infliximab, Intetumumab, Inolimomab, Inotuzumab ozogamicin, Ipilimumab, Iratumumab, Keliximab, Labetuzumab, Lebrikizumab, Lemalesomab, Lerdelimumab, Lexatumumab, Libivirumab, Lintuzumab, Lorvotuzumab mertansine, Lucatumumab, Lumiliximab, Mapatumumab, Maslimomab, Matuzumab, Mepolizumab, Metelimumab, Milatuzumab, Minretumomab, Mitumomab, Morolimumab, Motavizumab, Muromonab-CD3, Nacolomab tafenatox, Naptumomab estafenatox, Natalizumab, Nebacumab, Necitumumab, Nerelimomab, Nimotuzumab, Nofetumomab merpentan, Ocrelizumab, Odulimomab, Ofatumumab, Olaratumab, Omalizumab, Oportuzumab monatox, Oregovomab, Otelixizumab, Pagibaximab, Palivizumab, Panitumumab, Panobacumab, Pascolizumab, Pemtumomab, Pertuzumab, Pexelizumab, Pintumomab, Priliximab, Pritumomab, Rafivirumab, Ramucirumab, Ranibizumab, Raxibacumab, Regavirumab Reslizumab, Rilotumumab, Rituximab, Robatumumab, Rontalizumab, Rovelizumab, Ruplizumab, Satumomab pendetide, Sevirumab, Sibrotuzumab, Sifalimumab, Siltuximab, Siplizumab, Solanezumab, Sonepcizumab, Sontuzumab, Stamulumab, Sulesomab, Tacatuzumab tetraxetan, Tadocizumab, Talizumab, Tanezumab, Taplitumomab paptox, Tefibazumab, Telimomab aritox, Tenatumomab, Teneliximab, Teplizumab, Ticilimumab (tremelimumab), Tigatuzumab, Tocilizumab (atlizumab), Toralizumab, Tositumomab, Trastuzumab, Tremelimumab, Tucotuzumab celmoleukin, Tuvirumab, Urtoxazumab, Ustekinumab, Vapaliximab, Vedolizumab, Veltuzumab, Vepalimomab, Visilizumab, Volociximab, Votumumab, Zalutumumab, Zanolimumab, Ziralimumab, and Zolimomab aritox.

Examples of infusion therapy or injectable therapeutic proteins contemplated in the present invention include, but are not limited to, Tocilizumab (Roche/Actemra®), alpha-1 antitrypsin (Kamada/AAT), Hematide® (Affymax and Takeda, synthetic peptide), albinterferon alfa-2b (Novartis/Zalbin™), Rhucin® (Pharming Group, C1 inhibitor replacement therapy), tesamorelin (Theratechnologies/Egrifta, synthetic growth hormone-releasing factor), ocrelizumab (Genentech, Roche and Biogen), belimumab (GlaxoSmithKline/Benlysta®), pegloticase (Savient Pharmaceuticals/Krystexxa™), taliglucerase alfa (Protalix/Uplyso), agalsidase alfa (Shire/Replagal®), velaglucerase alfa (Shire).

Other examples of therapeutic proteins contemplated in the present invention include, but are not limited to, imiglucerase for the treatment of Gaucher's disease (e.g., CEREZYME™), a-galactosidase A (a-gal A) for the treatment of Fabry disease (e.g., agalsidase beta, FABRYZYME™), acid a-glucosidase (GAA) for the treatment of Pompe disease (e.g., alglucosidase alfa, rhGAA (e.g., LUMIZYME™, MYOZYME™), arylsulfatase B for the treatment of Mucopolysaccharidoses (e.g., laronidase, ALDURAZYME™ idursulfase, ELAPRASE™, arylsulfatase B, NAGLAZYME™).

As used herein, the terms "associated with," "conjugated," "linked," "attached," "tethered," and "complex" when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. The moieties can be connected via covalent or non-covalent interactions. In some instances, moieties are connected by covalent bonds. In some instances, moieties are connected by non-covalent interactions. In some embodiments, a sufficient number of weaker interactions can provide sufficient stability for moieties to remain physically associated under a variety of different conditions.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc.

The antisense oligonucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

The terms "nucleic acid" or "nucleic acid sequence", "nucleic acid molecule", "nucleic acid fragment" or "polynucleotide" may be used interchangeably with "gene", "mRNA encoded by a gene" and "cDNA".

The term "mRNA" or "mRNA molecule" refers to messenger RNA, or the RNA that serves as a template for protein synthesis in a cell. The sequence of a strand of mRNA is based on the sequence of a complementary strand of DNA comprising a sequence coding for the protein to be synthesized.

The term "siRNA" or "siRNA molecule" refers to small inhibitory RNA duplexes that induce the RNA interference (RNAi) pathway, where the siRNA interferes with the expression of specific genes with a complementary nucleotide sequence. siRNA molecules can vary in length (e.g., between 18-30 or 20-25 basepairs) and contain varying degrees of complementarity to their target mRNA in the antisense strand. Some siRNA have unpaired overhanging bases on the 5' or 3' end of the sense strand and/or the antisense strand. The term siRNA includes duplexes of two separate strands, as well as single strands that can form hairpin structures comprising a duplex region.

The term "amino acid" refers to a molecule containing both an amino group and a carboxyl group. Amino acids include alpha-amino acids and beta-amino acids, the structures of which are depicted below. In certain embodiments, an amino acid is an alpha amino acid.

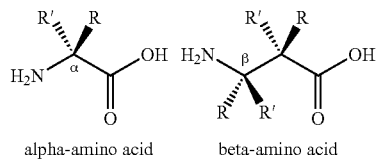

alpha-amino acid          beta-amino acid

Suitable amino acids include, without limitation, natural alpha-amino acids such as D- and L-isomers of the 20 common naturally occurring alpha-amino acids found in peptides (e.g., A, R, N, C, D, Q, E, G, H, I, L, K, M, F, P, S, T, W, Y, V, as provided below), unnatural alpha-amino acids natural beta-amino acids (e.g., beta-alanine), and unnatural beta-amino acids. Exemplary natural alpha-amino acids include L-alanine (A), L-arginine (R), L-asparagine (N), L-aspartic acid (D), L-cysteine (C), L-glutamic acid (E), L-glutamine (Q), glycine (G), L-histidine (H), L-isoleucine (I), L-leucine (L), L-lysine (K), L-methionine (M), L-phenylalanine (F), L-proline (P), L-serine (S), L-threonine (T), L-tryptophan (W), L-tyrosine (Y), and L-valine (V). Exemplary unnatural alpha-amino acids include D-arginine, D-asparagine, D-aspartic acid, D-cysteine, D-glutamic acid, D-glutamine, D-histidine, D-isoleucine, D-leucine, D-lysine, D-methionine, D-phenylalanine, D-proline, D-serine, D-threonine, D-tryptophan, D-tyrosine, D-valine, Di-vinyl, α-methyl-alanine (Aib), α-methyl-arginine, α-methyl-asparagine, α-methyl-aspartic acid, α-methyl-cysteine, α-methyl-glutamic acid, α-methyl-glutamine, α-methyl-histidine, α-methyl-isoleucine, α-methyl-leucine, α-methyl-lysine, α-methyl-methionine, α-methyl-phenylalanine, α-methyl-proline, α-methyl-serine, α-methyl-threonine, α-methyl-tryptophan, α-methyl-tyrosine, α-methyl-valine, norleucine, terminally unsaturated alpha-amino acids and bis alpha-amino acids (e.g., modified cysteine, modified lysine, modified tryptophan, modified serine, modified threonine, modified proline, modified histidine, modified alanine, and the like). There are many known unnatural amino acids any of which may be included in the peptides of the present invention. See for example, S. Hunt, *The Non-Protein Amino Acids: In Chemistry and Biochemistry of the Amino Acids*, edited by G. C. Barrett, Chapman and Hall, 1985.

As generally used herein, "radionuclide" refers to a radioactive nuclide (also referred to as "radioactive isotope" or "radioisotope"). Radioactive nuclides contain excess nuclear energy and are capable of undergoing radioactive decay to emit radiation (e.g., gamma radiation, alpha particles, beta particles) or internal conversion to eject an electron. Radionuclides can be used in radiolabeling and radioactive tracing.

As used herein, "Fluorophores" are fluorescent chemical compounds that emit light upon light excitation. Fluorophores contemplated in the present invention include, but are not limited to, dyes. Commonly recognized fluorophores include, but are not limited to, xanthene derivatives (e.g., fluorescein, rhodamine, Oregon green, eosin, Texas red), cyanine derivatives (e.g., cyanine, indocarbocyanine, oxacarbocyanine, thiacarbocyanine, merocyanine), squaraine derivatives and ring-substituted squaraines (e.g., Seta, SeTau, Square dyes), naphthalene derivatives (e.g., dansyl and prodan derivatives), coumarin derivatives, oxadiazole derivatives: (e.g., pyridyloxazole, nitrobenzoxadiazole, benzoxadiazole), anthracene derivatives (e.g., anthraquinones, including DRAQ5, DRAQ7, CyTRAK Orange), pyrene derivatives (e.g., cascade blue), oxazine derivatives (e.g., Nile red, Nile blue, cresyl violet, oxazine 170), acridine derivatives (e.g., proflavin, acridine orange, acridine yellow), arylmethine derivatives (e.g., auramine, crystal violet, malachite green), and tetrapyrrole derivatives (e.g., porphin, phthalocyanine, bilirubin). Examples of more recent fluorphores and their vendors include, but are not limited to, CF dye (Biotium), DRAQ and CyTRAK probes (BioStatus), BODIPY (Invitrogen), Alexa Fluor (Invitrogen), DyLight Fluor (Thermo Scientific, Pierce), Atto and Tracy (Sigma Aldrich), FluoProbes (Interchim), Abberior Dyes (Abberior), DY and MegaStokes Dyes (Dyomics), Sulfo Cy dyes (Cyandye), HiLyte Fluor (AnaSpec), Seta, SeTau and Square Dyes (SETA BioMedicals), Quasar and Cal Fluor dyes (Biosearch Technologies), SureLight Dyes (APC, RPE-PerCP, Phycobilisomes)(Columbia Biosciences), APC, APCXL, RPE, and BPE (Phyco-Biotech, Greensea, Prozyme, Flogen). Other examples of fluorophores contemplated in the present invention include, but are not limited to, hydroxycoumarin, aminocoumarin, methoxycoumarin, Cascade Blue, Pacific Blue, Pacific Orange, Lucifer yellow, NBD, R-Phycoerythrin (PE), PE-Cy5 conjugates (e.g., Cychrome, R670, Tri-Color, Quantum Red), PE-Cy7 conjugates, Red 613 (PE-Texas Red), PerCP (Peridinin chlorophyll protein), TruRed (PerCP-Cy5.5 conjugate), FluorX, Fluorescein, BODIPY-FL, Cy2, Cy3, Cy3B, Cy3.5, Cy5, Cy5.5, Cy7, TRITC, X-Rhodamine (XRITC), Lissamine Rhodamine B, Texas Red, Allophycocyanin (APC), and APC-Cy7 conjugates. Other examples of fluorophores include, but are not limited to, hoechst, DAPI, SYTOX Blue, Chromomycin A3, Mithramycin, YOYO-1, Ethidium Bromide, Acridine Orange, SYTOX Green, TOTO-1, TO-PRO-1 TOTO: Cyanine Dimer, TO-PRO: Cyanine Monomer, Thiazole Orange, CyTRAK Orange 5, Propidium Iodide (PI), LDS, 7-AAD (7-aminoactinomycin D), SYTOX Orange, TOTO-3, TO-PRO-3, DRAQ5, DRAQ7, Indo-1, Fluo-3, Fluo-4, DCFH (2'7'Dichorodihydrofluorescein), DHR (Dihydrorhodamine), and SNARF. Fluorophores also include fluorescent proteins, examples of which include, but are not limited to, green fluorescent protein (e.g., wild-type, Y66H mutation, Y66F mutation, Y66W mutation, S65A mutation, S65C mutation, S65L mutation, TurboGFP, TagGFP, S65T mutation, GFPuv, EGFP), EBFP, EBFP2, Azurite, T-Sapphire, Cerulean, mCFP, mTurquoise2, ECFP, CyPet, mKeima-Red, TagCFP, AmCyan1, mTFP1, Midoriishi Cyan, Emerald, Azami Green, ZsGreen1, TagYFP, EYFP, Topaz, Venus, mCitrine, Ypet, TurboYFP, ZsYellow1, Kusabira Orange, mOrange, Allophycocyanin (APC), mKO, TurboRFP, tdTomato, TagRFP, DsRed monomer, DsRed2, mStrawberry, TurboFP602, AsRed2, mRFP1, J-Red, R-phycoerythrin (RPE), B-phycoerythrin (BPE), mCherry, HcRed1, Katusha, P3 (phycobilisome complex[6]), Peridinin Chlorophyll (PerCP), mKate (TagFP635), TurboFP635, mPlum, and mRaspberry.

As used herein, "chemiluminescent agents" refers to molecules that release energy in the form of heat or light as a result of a chemical reaction.

As used herein, "hapten" refers to a molecule (e.g., small molecule) that triggers an immune response (e.g., production of antibodies) when bound to a carrier molecule such as a protein.

As used herein, "diagnostic agent" refers to molecule that can be used to visualize or characterize a certain biological process and/or to diagnose a certain condition in a subject.

As generally defined herein, "particles" include any organic or inorganic particles. Specific examples of particles include, but are more limited to, organic nanoparticles such as lipid nanoparticles, liposomes, and micelles. Other examples of particles include, but are not limited to, metallic nanoparticles.

As used herein, "colorimetric labels" refers to any molecule that can be observed or quantified by colorimetry. "Colorimetry" refers to the detection (e.g., quantification) of a molecule or compound by measuring its absorbance of a specific wavelength of light.

As used herein, "fatty acid" refers to a carboxylic acid with a saturated or unsaturated, substituted or unsubstituted, branched or unbranched aliphatic chain. In certain embodiments, the aliphatic chain comprises 4 to 28 carbon atoms. In certain embodiments, the aliphatic chain of the fatty acid comprises more than 28 carbon atoms. Derivatives of fatty acid are also contemplated in the invention (e.g., ester and amide derivatives). As defined herein, "short-chain fatty acids" are fatty acids with aliphatic tails of fewer than six carbons (e.g., butyric acid). As defined herein, "medium-chain fatty acids" are fatty acids with aliphatic tails of 6-12 carbons. As defined herein, "long-chain fatty acids" are fatty acids with aliphatic tails 13 to 21 carbons. As also defined herein, "very long chain fatty acids" are fatty acids with aliphatic tails longer than 22 carbons. Examples of unsaturated fatty acids include, but are not limited to, myristoleic acid, palmitoleic acid, sapienic, oleic acid, elaidic acid, vaccenic acid, linoleic acid, linoelaidic acid, α-linolenic acid, arachidonic acid, eicosapentaenoic acid, and erucic acid, docosahexaenoic acid. Examples of saturated fatty acids include, but are not limited to, caprylic acid, capric acid, lauric acid, myristic acid, palmitic acid, stearic acid, arachidic acid, behenic acid, lignoceric acid, and cerotic acid.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5\ H_2O$)), and polyhydrates (x is a number greater than 1, e.g., dihydrates ($R \cdot 2\ H_2O$) and hexahydrates ($R \cdot 6\ H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations. It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. C1-C8 alkyl, C2-C8 alkenyl, C2-C8 alkynyl, aryl, C7-C12 substituted aryl, and C7-C12 arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

Medical Conditions

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

A "diabetic condition" (also referred to as "diabetes") refers to diabetes and pre-diabetes. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. Type I diabetes results from the body's failure to produce insulin, and presently requires the person to inject insulin or wear an insulin pump. Type II diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes. All forms of diabetes increase the risk of long-term complications. These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antitrypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beckwith-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syndrome, colon cancer, congenital adrenal hyperplasia, Cornelia de Lange syndrome, Costello syndrome, Cowden syndrome, craniofrontonasal dysplasia, Crigler-Najjar syndrome, Creutzfeldt-Jakob disease, cystic fibrosis, deafness, depression, diabetes, diastrophic dysplasia, DiGeorge syndrome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholesterolemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syndrome), Gorlin syndrome, Hailey-Hailey disease, hemihypertrophy, hemochromatosis, hemophilia, hereditary motor and sensory neuropathy (HMSN), hereditary non polyposis colorectal cancer (HNPCC), Huntington's disease, immunodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endocrine neoplasia, multiple sclerosis, muscular dystrophy, myotrophic lateral sclerosis, myotonic dystrophy, neurofibromatosis, Niemann-Pick disease, Noonan syndrome, obesity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syndrome, Sanfilippo syndrome, schizophrenia, severe combined immunodeficiency, sickle cell anemia, spina *bifida*, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syndrome, von Hippel-Lindau syndrome, Waardenburg syndrome, Weaver syndrome, Werner syndrome, Williams syndrome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology;* Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., FGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "spleen disease" refers to a disease of the spleen. Example of spleen diseases include, but are not limited to, splenomegaly, spleen cancer, asplenia, spleen trauma, idiopathic purpura, Felty's syndrome, Hodgkin's disease, and immune-mediated destruction of the spleen.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; bbrain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome;

olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina *bifida*; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

A "painful condition" includes, but is not limited to, neuropathic pain (e.g., peripheral neuropathic pain), central pain, differentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawal symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

The term "psychiatric disorder" refers to a disease of the mind and includes diseases and disorders listed in the *Diagnostic and Statistical Manual of Mental Disorders—Fourth Edition (DSM-IV)*, published by the American Psychiatric Association, Washington D. C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, cannabis dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

A "cardiovascular disease" (CVD) refers to a disease that involves the heart or blood vessels. Cardiovascular disease includes coronary artery diseases (e.g., angina and myocardial infarction (i.e., heart attack). Other types of cardiovascular disease include, but are not limited to, stroke, hypertensive heart disease, rheumatic heart disease, cardiomyopathy, atrial fibrillation, congenital heart disease, endocarditis, aortic aneurysms, peripheral artery disease and venous thrombosis. CVDs that affect the blood vessels (i.e., "vascular diseases") include, but are not limited to, coronary artery disease (i.e., coronary heart disease or ischemic heart disease), peripheral arterial disease, cerebrovascular disease (e.g., stroke), renal artery stenosis, and aortic aneurysm. CVDs that affect the heart include, but are not limited to, cardiomyopathy, hypertensive heart disease, heart failure, pulmonary heart disease, cardiac dysrhythmias, inflammatory heart disease (e.g., endocarditis, inflammatory cardiomegaly, myocarditis), valvular heart disease, congenital heart disease, and rheumatic heart disease.

An "infectious disease" refers to any disease caused by a pathogen (i.e., pathogenic microorganisms). An infectious disease may be caused by bacteria, viruses, parasites, or fungi. In certain embodiments, the infectious disease is a bacterial infection. In certain embodiments, the infectious disease is a viral infection.

An "endocrine disease" refers to a disease involving the endocrine system. Examples of endocrine diseases include, but are not limited to, adrenal disorders (e.g., adrenal insufficiency (e.g., Addison's disease, mineralocorticoid deficiency), adrenal hormone excess (e.g., Conn's syndrome, Cushing's syndrome, glucocorticoid remediable aldosteronism (GRA), pheochromocytoma), congenital adrenal hyperplasia (i.e., adrenogenital syndrome), adrenocortical carcinoma)), glucose homeostasis disorders (e.g., diabetes mellitus, hypoglycemia, glucagonoma), thyroid disorders (e.g., goiter, hyperthyroidism (e.g., Graves-Basedow disease, toxic multinodular goiter), hypothyroidism, thyroiditis (e.g., Hashimoto's thyroiditis), thyroid cancer, thyroid hormone resistance), calcium homeostasis disorders and Metabolic bone diseases (e.g., parathyroid gland disorders (e.g., primary hyperparathyroidism, secondary hyperparathyroidism, tertiary hyperparathyroidism, hypoparathyroidism (e.g., pseudohypoparathyroidism)), osteoporosis, psteitis deformans (i.e., Paget's disease of bone), rickets, osteomalacia), pituitary gland disorders (e.g., diabetes insipidus, hypopituitarism (or panhypopituitarism), pituitary tumors (e.g., pituitary adenomas, prolactinoma (or hyperprolactinemia), acromegaly, gigantism, Cushing's disease))), sex hormone disorders (e.g., disorders of sex development or intersex disorders (e.g., hermaphroditism, gonadal dysgenesis, androgen insensitivity syndromes), hypogonadism (gonadotropin deficiency) (e.g., Kallmann syndrome, Klinefelter syndrome, Turner syndrome, ovarian failure (i.e., premature menopause), testicular failure), disorders of puberty (e.g., delayed puberty, precocious puberty), menstrual function or fertility disorders (e.g., amenorrhea, polycystic ovary syndrome)), and tumours of the endocrine glands.

DETAILED DESCRIPTION OF CERTAIN EMBODIMENTS

Therapeutic agents, diagnostic agents, and imaging agents have an array of attendant complications that arise from poor chemical and/or structural stability that can lead to the agent being converted into an inactive and/or potentially immunogenic form. Extensive efforts have been devoted to the development of excipients, labels, and tags for use in the formulation of agents to confer improved stability, solubility, duration of action, or pharmacological properties. More generally, the modification of biomolecules, small molecules, and other agents of via conjugation of tags or labels is of great importance. One approach to tagging drugs or other agents is through direct covalent modification. Alternative means of modifying biomolecules that do not rely on covalent bonding are desired; in particular, site-specific non-covalent complexation. Supramolecular chemistry utilizes specific, directional, reversible, non-covalent molecular recognition motifs in order to achieve organization of molecules. As described in the present invention, supramolecular chemistry can be used to bind agents to excipients, labels, and other tags.

The present invention provides useful supramolecular complexes comprising an agent associated with a tag, wherein the agent is specifically bound to a host via non-covalent guest-host interactions, and wherein the host is conjugated to the tag. The present invention also provides methods and compounds useful in preparing the supramolecular complexes described herein, and methods of treating diseases using the supramolecular complexes.

Supramolecular Complexes

The present invention provides supramolecular complexes comprising an agent associated with a tag, wherein:
  (1) the agent is specifically bound to a host via non-covalent interactions; and
  (2) the host is conjugated to the tag.

It is to be understood that the agent that is associated with a tag can be anything. In certain embodiments, the agent that is associated with a tag is selected from the group consisting of biomolecules, small molecule drugs, imaging agents, and diagnostic agents. In certain embodiments, the agent is a small molecule. In certain embodiments, the agent is a therapeutic small molecule. In certain embodiments, the agent is a biomolecule. In certain embodiments, the agent is a therapeutic biomolecule. In certain embodiments, the agent is a biomolecule selected from the group consisting of proteins, peptides, nucleic acids, polysaccharides, and lipids. In certain embodiments, the agent is a peptide. In certain embodiments, the agent is a protein. In certain embodiments, the agent is an enzyme. In certain embodiments, the agent is an antibody or antibody fragment. In certain embodiments, the agent is a monoclonal antibody. In certain embodiments, the agent is a human antibody or a humanized antibody. In certain embodiments, the agent is an antibody directed against human CD20. Examples of anti-CD20 antibodies include, but are not limited to, rituximab, obinutuzumab, ibritumomab tiuxetan, tositumomab, ofatumumab (Genmab), obinutuzumab (Gazyva), ocaratuzumab, ocrelizumab, and IMMU-106 (veltuzumab). In certain embodiments, the agent is an antibody useful in the treatment of cancer (e.g., trastuzumab, rituximab). In certain embodiments, the agent is a polysaccharide. In certain embodiments, the agent is a lipid. In certain embodiments, the agent is a nucleic acid. (e.g., DNA, RNA, and hybrids thereof). In certain embodiments, the agent is a protein. In certain embodiments, the agent is a therapeutic protein. In certain embodiments, the agent is a modified protein. In certain embodiments, the agent is a native or wild-type protein. In certain embodiments, the agent is GLP-1 or an analogue thereof. In certain embodiments, the agent is an interferon. In certain embodiments, the agent is a growth factor (e.g., BMP-2, VEGF, FGF-2, PDGF). In certain embodiments, the agent is a growth hormone. In certain embodiments, the agent is glucagon. In certain embodiments, the agent is insulin. In certain embodiments, the agent is a derivative of insulin. In certain embodiments, the agent is native or wild-type insulin.

As described herein, the agent is specifically bound to a host via non-covalent interactions. It is to be understood that when the agent binds to the host, a "supramolecular complex" results. In certain embodiments, the host is a macrocycle. In certain embodiments, the macrocyclic host is selected from the group consisting of cucurbiturils, cyclodextrins, calixarenes, pillararenes, porphyrins, metallacrowns, crown ethers, cyclotriveratrylenes, cryptophanes, cyclophanes, and carcerands. In certain embodiments, the macrocyclic host is a cyclophane. In certain embodiments, the macrocyclic host is a cyclophane comprising paraquat moieties. In certain embodiments, the host is cyclobis(paraquat-p-phenylene). In certain embodiments, the macrocyclic host is a cucurbituril, wherein cucurbituril is as defined herein. In certain embodiments, the host is an optionally substituted acyclic cucurbituril. See, e.g., Isaacs et al. *Nat. Chem.* 2012, 4, 503-510. In certain embodiments, the macrocyclic host is an optionally substituted cucurbituril. In certain embodiments, the macrocyclic host is a substituted cucurbituril. In certain embodiments, the host is an optionally substituted cucurbit[n]uril (CB[n]), wherein n is an integer between 5-10, inclusive. In certain embodiments, n is 5. In certain embodiments, n is 6. In certain embodiments, n is 7. In certain embodiments, n is 8. In certain embodiments, n is 9. In certain embodiments, n is 10. In certain embodiments, n is 7, and the host is optionally substituted cucurbit[7]uril (CB[7]).

As generally defined herein, "host" or "host molecule" refers to a moeity which forms a complex with a second moiety (generally defined herein as "guest" or "guest moiety") via non-covalent interactions. See, e.g., Lehn et al. *Angewandte Chemie International Edition in English* 1988, 27(1): 89-112; Lehn et al. *Proc Natl Acad Sci USA* 2002, 99(8): 4763-4768; Schneider et al. *Angew Chem Int Edit* 1991, 30(11): 1417-1436. See, e.g., Liu et al. *Journal of the American Chemical Society* 2005, 127(45): 15959-15967; Del Valle et al. *Process Biochem* 2004, 39(9): 1033-1046; Biedermann et al. *Journal of the American Chemical Society* 2012, 134(37): 15318-15323. See, e.g., Davis et al. *Nat Rev Drug Discov* 2004, 3(12): 1023-1035; Uekama et al. *Crit Rev Ther Drug* 1987, 3(1): 1-40. It is to be understood that when a host binds to a guest, a supramolecular complex is formed. A host may bind to a guest via any combination of non-covalent interactions. Examples of non-covalent interactions include, but are not limited to, electrostatic interactions, π-interactions, hydrogen bonds, ionic bonds, van der Waals forces, and hydrophobic interactions. In some instances, the host is acyclic. In some instances, a host is a macrocycle (also referred to as a "inclusion compound"), and the guest binds inside the cavity of the macrocycle. Examples of macrocyclic hosts include, but are not limited to, cucurbiturils, cyclodextrins, calixarenes, pillararenes, porphyrins, metallacrowns, crown ethers, cyclotriveratrylenes, cryptophanes, cyclophanes and carcerands.

As generally defined herein, "cucurbituril" refers to a macrocyclic polymer comprising glycouril monomers linked by methylene (—CH$_2$—) bridges. A cucurbituril may be referred to as "cucurbit[n]uril" or "CB[n]", wherein n is the number of glycouril monomers present in the macrocycle. In certain embodiments, the cucurbituril In certain embodiments, the cucurbituril comprises 5 glycouril units (cucurbit[5]uril or CB[5]). In certain embodiments, the cucurbituril comprises 6 glycouril units (cucurbit[6]uril or CB[6]). In certain embodiments, the cucurbituril comprises 7 glycouril units (cucurbit[7]uril or CB[7]). In certain embodiments, the cucurbituril comprises 8 glycouril units (cucurbit[8]uril or CB[8]). In certain embodiments, the cucurbituril comprises 9 glycouril units (cucurbit[9]uril or CB[9]). In certain embodiments, the cucurbituril comprises 10 glycouril units (cucurbit[10]uril or CB[10]). In certain embodiments, the cucurbituril is substituted. In certain embodiments, the cucurbituril is unsubstituted. Cucurbiturils, as generally defined herein, are of the following formula:

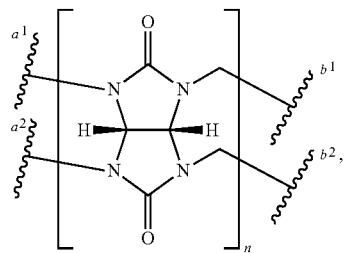

wherein $a^1$ indicates the point of attachment to $b^1$; $a^2$ indicates the point of attachment to $b^2$; and n is an integer between 2-20, inclusive. The formula above may be optionally substituted. "Optionally substituted" refers to a hydrogen atom being replaced with a substituent described herein. For example, an unsubstituted cucurbituril comprising 7 glycouril units (cucurbit[7]uril or CB[7]) is of the following formula:

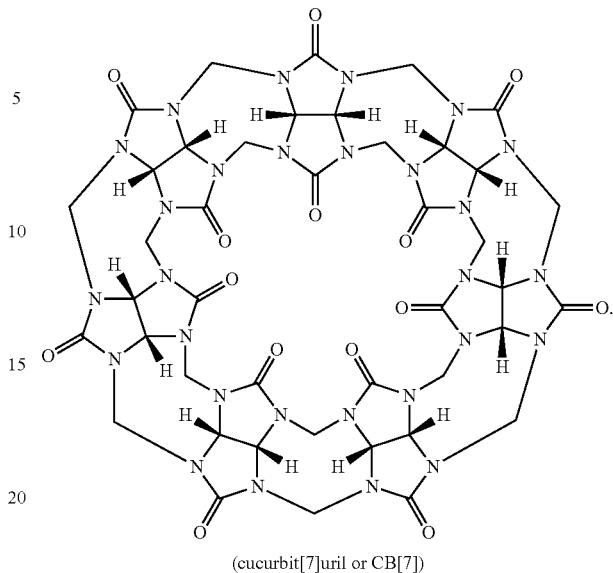

(cucurbit[7]uril or CB[7])

As generally defined herein, "cyclodextrin" refers to a macrocyclic polymer comprising sugar monomers (often referred to as "cyclic oligosaccharide" or "cycloamylose"). In some instances, a cyclodextrin comprises 5 or more α-D-glucopyranoside units. Typical cyclodextrins are made up of 6 glucose monomers (alpha-cyclodextrin), 7 glucose monomers (beta-cyclodextrin), or 8 glucose monomers (gamma-cyclodextrin).

The supramolecular complexes described herein comprise an agent associated with a tag. In certain embodiments, the tag is selected from the group consisting of polymers, therapeutic agents, targeting agents, radionuclides, fluorophores, chromophores, phosphorescent agents, dyes, chemiluminescent agents, particles, colorimetric labels, magnetic labels, haptens, biomolecules, small molecules, fatty acids, hydrocarbon chains, excipients, and diagnostic agents. The tag may be useful for stabilizing, solubilizing, modulating the duration of action of the agent, or improving the pharmacological properties of the agent. In certain embodiments, the tag is a an excipient (e.g., pharmaceutically acceptable excipient). Examines of pharmaceutically acceptable excipients are provided elsewhere herein. In certain embodiments, the tag is a polymer. In certain embodiments, the tag is a polyboronic acid or a polyboronic ester. In certain embodiments, the tag is a polyether. In certain embodiments, the tag is a polyglycol. In certain embodiments, the tag is polyethylene glycol (PEG). In certain embodiments, the tag is a copolymer of PEG. In certain embodiments, the tag is PEG, and the PEG has a molecular weight <1 kDa. In certain embodiments, the PEG has a molecular weight between 1-10 kDa, inclusive. In certain embodiments, the PEG has a molecular weight of approximately 5 kDa. In certain embodiments, the PEG has a molecular weight between 5-10 kDa, inclusive. In certain embodiments, the PEG has a molecular weight of approximately 10 kDa. In certain embodiments, In certain embodiments, the PEG has a molecular weight between 10-30 kDa, inclusive. In certain embodiments, the PEG has a molecular weight of approximately 30 kDa. In certain embodiments, the PEG has a molecular weight >30 kDa. In certain embodiments, the PEG has a molecular weight under 100 kDa.

The supramolecular complexes described herein comprise an agent bound to a host via non-covalent interactions. In certain embodiments, the non-covalent interactions are guest-host interactions. In certain embodiments, the non-covalent interactions involve electrostatic interactions, π-interactions, van der Waals forces, or hydrophobic interactions. In certain embodiments, the non-covalent interactions involve hydrogen bonding. In certain embodiments, the non-covalent interactions are site-specific. In certain embodiments, the non-covalent interactions are reversible.

It is to be understood that the supramolecular complexes described herein comprise an agent which comprises one or more guest moieties capable of binding to a host. In certain embodiments, the guest moiety is an amino acid. In certain embodiments, the agent is a biomolecule (e.g., peptide or protein) comprising one or more amino acids, and the host binds to an amino acid of the biomolecule. In certain embodiments, the agent is a protein, and the host binds to an amino acid of the protein. In certain embodiments, the host binds an amino acid selected from the group consisting of phenylalanine, tryptophan, and tyrosine. In certain embodiments, the host binds to phenylalanine. In certain embodiments, the host binds an N-terminal amino acid of the protein. In certain embodiments, the host binds to an N-terminal phenylalanine, tryptophan, or tyrosine of the protein. In certain embodiments, the host binds to an N-terminal phenylalanine of the protein. In certain embodiments, the protein is insulin, and the host binds to a phenylalanine of insulin. In certain embodiments, the protein is insulin and the host binds to the B1 phenylalanine of insulin. In certain embodiments, the host that binds to an amino acid of insulin is an optionally substituted cucurbituril. In certain embodiments, the host that binds to an amino acid of insulin is an optionally substituted cucurbit[7]uril.

In particular embodiments of the invention, the agent associated with a tag is a biomolecule, the host is a macrocycle, and the tag is a polymer. In certain embodiments, the agent associated with a tag is a protein, the host is an optionally substituted cucurbituril, and the tag conjugated to the host is a polymer. In certain embodiments, the agent associated with a tag is a protein, the host is an optionally substituted cucurbituril, and the tag conjugated to the host is an excipient (e.g., pharmaceutically acceptable excipient). In certain embodiments, the agent associated with a tag is a protein, the host is an optionally substituted cucurbituril, and the tag conjugated to the host is PEG. In certain embodiments, the agent associated with a tag is a protein, the host is an optionally substituted cucurbituril, and the tag conjugated to the host is an excipient. In certain embodiments, the agent associated with a tag is a protein, the host is an optionally substituted cucurbituril, and the tag conjugated to the host is a polymer. In certain embodiments, the protein is insulin, the host is an optionally substituted cucurbituril, and the tag is a polymer. In certain embodiments, the protein is insulin, the host is an optionally substituted cucurbituril, and the tag is an excipient. In certain embodiments, the protein is insulin, the host is an optionally substituted cucurbituril, and the tag is PEG. In certain embodiments, the protein is insulin, the host is an optionally substituted cucurbit[7]uril, and the tag is a polymer. In certain embodiments, the protein is insulin, the host is an optionally substituted cucurbit[7]uril, and the tag is an excipient. In certain embodiments, the protein is insulin, the host is an optionally substituted cucurbit[7]uril, and the tag is PEG. In certain embodiments, the protein is insulin, the host is macrocycle, and the tag is polyboronic acid or polyboronic ester. In certain embodiments, the protein is insulin, the host is an optionally substituted cucurbituril, and the tag is polyboronic acid or polyboronic ester.

In certain embodiments, the protein associated with a tag is glucagon, the host is a macrocycle, and the tag is a polymer. In certain embodiments, the protein associated with a tag is glucagon, the host is a macrocycle, and the tag is an excipient. In certain embodiments, the protein is glucagon, the host is a macrocycle, and the tag is PEG. In certain embodiments, the protein is glucagon, the host is an optionally substituted cucurbituril, and the tag is a polymer. In certain embodiments, the protein is glucagon, the host is an optionally substituted cucurbituril, and the tag is an excipient. In certain embodiments, the protein is glucagon, the host is an optionally substituted cucurbituril, and the tag is PEG. In certain embodiments, the protein is glucagon, the host is an optionally substituted cucurbit[7]uril, and the tag is a polymer. In certain embodiments, the protein is glucagon, the host is an optionally substituted cucurbit[7]uril, and the tag is an excipient. In certain embodiments, the protein is glucagon, the host is an optionally substituted cucurbit[7]uril, and the tag is PEG. In certain embodiments, the protein is glucagon, the host is macrocycle, and the tag is polyboronic acid or polyboronic ester. In certain embodiments, the protein is glucagon, the host is an optionally substituted cucurbituril, and the tag is polyboronic acid or polyboronic ester.

In certain embodiments, the agent associated with a tag is an antibody, the host is a macrocycle, and the tag is a polymer. In certain embodiments, the agent is an anti-CD20 antibody, the host is a macrocycle, and the tag is PEG. In certain embodiments, the agent associated with a tag is an anti-CD20 protein, the host is an optionally substituted cucurbituril, and the tag conjugated to the host is a polymer. In certain embodiments, the agent associated with a tag is an anti-CD20 protein, the host is an optionally substituted cucurbituril, and the tag conjugated to the host is an excipient. In certain embodiments, the agent associated with a tag is an anti-CD20 protein, the host is an optionally substituted cucurbituril, and the tag conjugated to the host is PEG. In certain embodiments, the agent is an anti-CD20 antibody, the host is an optionally substituted cucurbit[7]uril, and the tag is PEG. In certain embodiments, the agent is an anti-CD20 antibody, the host is an optionally substituted cucurbit[7]uril, and the tag is a polymer. In certain embodiments, the agent is Rituximab, the host is cucurbit[7]uril, and the tag is a polymer. In certain embodiments, the agent is Rituximab, the host is cucurbit[7]uril, and the tag is PEG.

The supramolecular complexes described herein comprise a host conjugated to a tag. In certain embodiments, the host is directly conjugated to the tag (i.e., via a covalent bond). In certain embodiments, the host is conjugated to the tag via a linker.

In certain embodiments, the linker is a hydrocarbon chain. In certain embodiments, the linker is a polymer (e.g., polyethylene). In certain embodiments, the linker is an amino acid or peptide linker. In certain embodiments, the linker comprises a triazole. In certain embodiments, the linker comprises an amide. In certain embodiments, the linker comprises a disulfide. In certain embodiments, the linker comprises an ester. In certain embodiments, the linker comprises a thioether. In certain embodiments, the linker comprises a carbonate. In certain embodiments, the linker comprises a carbamate. In certain embodiments, the linker comprises a thiourea.

In certain embodiments, the linker is selected from the group consisting of optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, optionally substituted acylene, and combinations thereof.

In certain embodiments, the host is conjugated to a tag via a linker of Formula (L-1):

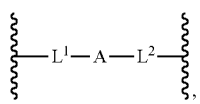
(L-1)

wherein:

each of $L^1$ and $L^2$ is independently a bond, optionally substituted alkylene, or optionally substituted heteroalkylene; and A is a bond, optionally substituted heterocyclyl, or optionally substituted heteroaryl.

As generally defined herein, each of $L^1$ and $L^2$ is independently a bond, optionally substituted alkylene, or optionally substituted heteroalkylene. In certain embodiments, at least one of $L^1$ and $L^2$ is a bond. In certain embodiments, both $L^1$ and $L^2$ are bonds. In certain embodiments, at least one of $L^1$ and $L^2$ is optionally substituted alkylene. In certain embodiments, both $L^1$ and $L^2$ are optionally substituted alkylene. In certain embodiments, at least one of $L^1$ and $L^2$ is optionally substituted heteroalkylene. In certain embodiments, both $L^1$ and $L^2$ are optionally substituted heteroalkylene. In certain embodiments, $L^1$ is optionally substituted alkylene and $L^2$ is optionally substituted heteroalkylene.

As generally defined herein, A is a bond, optionally substituted heterocyclyl, or optionally substituted heteroaryl. In certain embodiments, A is a bond. In certain embodiments, A is optionally substituted heterocyclyl. In certain embodiments, A is optionally substituted heteroaryl. In certain embodiments, A is optionally substituted five-membered heteroaryl. In certain embodiments, A is optionally substituted triazole. In certain embodiments, A is a polycyclic ring system. In certain embodiments, A is a tetracyclic ring system. In certain embodiments, A is a tetracyclic ring system comprising a triazole moiety.

In certain embodiments, $L^1$ is optionally substituted alkylene, $L^2$ is optionally substituted heteroalkylene, and A comprises a triazole moiety.

In certain embodiments, the host is conjugated to the tag via linker of Formula (L-2a) or (L-2b):

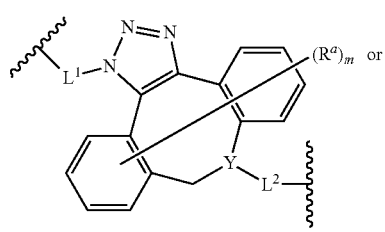
(L-2a)

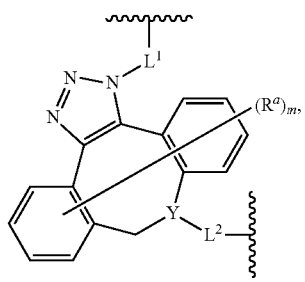
(L-2b)

wherein:

each of $L^1$ and $L^2$ is independently a bond, optionally substituted alkylene or optionally substituted heteroalkylene; and Y is $CR^a$ or N;

m is an integer from 0-10, inclusive;

each instance of $R^a$ is independently hydrogen, halogen, optionally substituted alkyl, optionally substituted heteroalkyl, optionally substituted alkenyl, optionally substituted alkynyl, optionally substituted acyl, optionally substituted carbocyclyl, optionally substituted heterocyclyl, optionally substituted aryl, optionally substituted heteroaryl, optionally substituted acyl, $-OR^{aa}$, $-SR^{aa}$, $-N(R^{aa})_2$, $-NO_2$, or $-CN$, or two $R^a$ attached to adjacent atoms are joined to form an optionally substituted carbocyclyl, optionally substituted heterocyclyl, optionally substituted aryl, optionally substituted heteroaryl ring;

each occurrence of $R^{aa}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, or a nitrogen protecting group, or two $R^{aa}$ are joined to form an optionally substituted heterocyclic or optionally substituted heteroaryl ring.

In certain embodiments, the linker is of Formula the linker is of Formula (L-3a) or (L-3b):

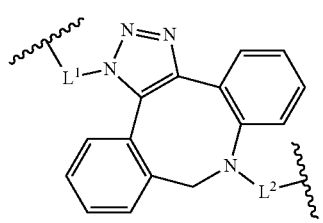
(L-3a)

or

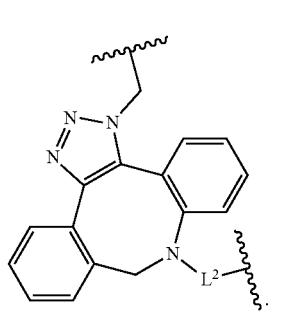
(L-3b)

In certain specific embodiments, the linker is of one of the following formulae:

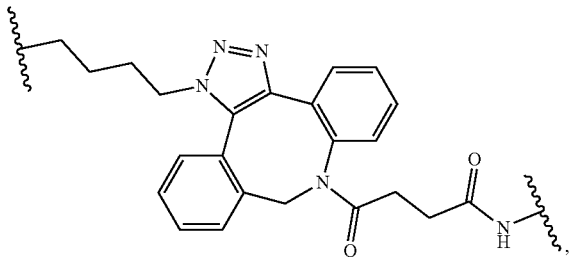

(L4-a)

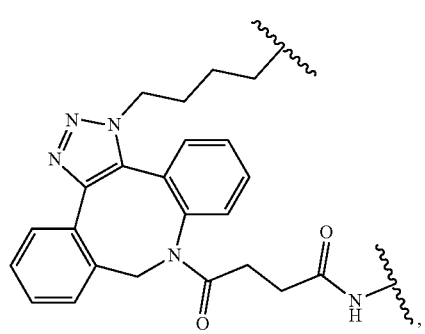

(L4-b)

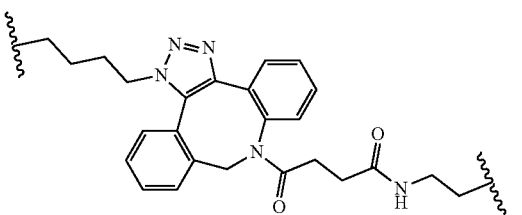

(L4-c)

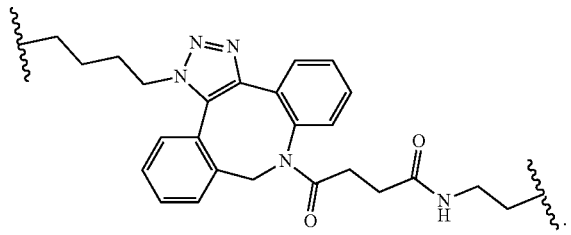

(L4-d)

The present invention provides supramolecular complexes comprising an agent associated with a tag. In certain embodiments, the tag improves the stability of the agent. In certain embodiments, the tag improves the solubility of the agent. In certain embodiments, the agent is a therapeutic agent, and the tag modulates the duration of action of the therapeutic agent. In certain embodiments, the tag improves the pharmacological properties of the agent. In particular embodiments of the present invention, the agent is a biomolecule, and the tag helps to stabilize the biomolecule. In certain embodiments, the agent is a therapeutic biomolecule, and the tag modulates the duration of action of the biomolecule. In certain embodiments, the agent is a therapeutic biomolecule, and the tag improves the pharmacological properties of the biomolecule. In certain embodiments, the agent is a biomolecule, and the tag is a polymer. In certain embodiments, the agent is a biomolecule, and the tag is an excipient. In certain embodiments, the agent is a biomolecule, and the tag is polyethylene glycol (PEG). In certain embodiments, the PEGylated biomolecule exhibits greater stability and/or improved duration of action compared with the biomolecule in its wild type or unmodified form. In certain embodiments, the biomolecule is a protein, and the tag is a polymer. In certain embodiments, the protein is a therapeutic protein and the tag is a polymer. In certain embodiments, the agent is a protein and the tag is a polymer. In certain embodiments, the agent is a protein and the tag is an excipient. In certain embodiments, the agent is a protein and the tag is a PEG. In certain embodiments, the protein is insulin and the tag is a polymer. In certain embodiments, the protein is insulin and the tag is an excipient. In certain embodiments, the protein is insulin and the tag is PEG. In certain embodiments, the PEGylated insulin exhibits greater stability and/or improved or sustained duration of action compared with insulin in its native or unmodified form. In certain embodiments, the protein is glucagon and the tag is a polymer. In certain embodiments, the protein is glucagon and the tag is an excipient. In certain embodiments, the protein is glucagon and the tag is PEG. In certain embodiments, the PEGylated glucagon exhibits greater stability and/or improved or sustained duration of action compared with glucagon in its native or unmodified form. In certain embodiments, the agent is an antibody and the tag is a polymer. In certain embodiments, the agent is an antibody and the tag is an excipient. In certain embodiments, the agent is an antibody and the tag is PEG. In certain embodiments, the PEGylated antibody exhibits greater stability and/or improved or sustained duration of action compared with the antibody in its native or unmodified form. In certain embodiments, the agent is an anti-CD20 antibody and the tag is an excipient. In certain embodiments, the agent is an anti-CD20 antibody and the tag is PEG. In certain embodiments, the PEGylated anti-CD20 antibody exhibits greater stability and/or improved or sustained duration of action compared with the antibody in its native or unmodified form.

Host-Tag Conjugates

The present invention also provides compounds which are useful in preparing the supramolecular complexes described herein. In general, these compounds comprise a host conjugated to a tag (referred to herein as "host-tag conjugates"). In certain embodiments, the host is a macrocycle. In certain embodiments, the macrocyclic host is selected from the group consisting of cucurbiturils, cyclodextrins, calixarenes, pillararenes, porphyrins, metallacrowns, crown ethers, cyclotriveratrylenes, cryptophanes, and carcerands. In certain embodiments, the macrocyclic host is a cucurbituril, wherein cucurbituril is as defined herein. In certain embodiments, the macrocyclic host is an optionally substituted cucurbituril. In certain embodiments, the macrocyclic host is a substituted cucurbituril. In certain embodiments, the host is an optionally substituted cucurbit[n]uril (CB[n]), wherein n is an integer between 5-10, inclusive. In certain embodiments, n is 5. In certain embodiments, n is 6. In certain embodiments, n is 7. In certain embodiments, n is 8. In certain embodiments, n is 9. In certain embodiments, n is 10. In certain embodiments, n is 7, and the host is optionally substituted optionally substituted cucurbit[7]uril (CB[7]).

In certain embodiments, the tag is selected from the group consisting of polymers, therapeutic agents, targeting agents, radionuclides, fluorophores, chromophores, phosphorescent agents, dyes, chemiluminescent agents, particles, colorimetric labels, magnetic labels, haptens, biomolecules, fatty acids, hydrocarbon chains, small molecules, and diagnostic agents. In certain embodiments, the tag is a polymer. In certain embodiments, the tag is a polyboronic acid or a polyboronic ester. In certain embodiments, the tag is a polyether. In certain embodiments, the tag is a polyglycol. In certain embodiments, the tag is polyethylene glycol (PEG). The PEG can be of any molecular weight.

In certain embodiments, the host is conjugated to the tag via a linker. In certain embodiments, the linker is selected from the group consisting of optionally substituted alkylene, optionally substituted heteroalkylene, optionally substituted alkenylene, optionally substituted heteroalkenylene, optionally substituted alkynylene, optionally substituted heteroalkynylene, optionally substituted carbocyclylene, optionally substituted heterocyclylene, optionally substituted arylene, optionally substituted heteroarylene, optionally substituted acylene, and combinations thereof.

In certain embodiments, the linker is a bond or optionally substituted aliphatic. In certain embodiments, the linker is a bond. The linker is optional, and the tag may be directly attached to the host. In certain embodiments, the linker is a hydrocarbon chain. In certain embodiments, the linker is a polymer (e.g., polyethylene). In certain embodiments, the linker is an amino acid or peptide linker. In certain embodiments, the linker comprises a triazole. In certain embodiments, the linker comprises an amide. In certain embodiments, the linker comprises a disulfide. In certain embodiments, the linker comprises an ester. In certain embodiments, the linker comprises a thioether. In certain embodiments, the linker comprises a carbonate. In certain embodiments, the linker comprises a carbamate. In certain embodiments, the linker comprises a thiourea.

In certain embodiments, the host-tag conjugate comprises a cucurbituril conjugated to a polymer. In certain embodiments, the cucurbituril is CB[7], and the polymer is PEG.

In certain embodiments, a compound comprising a host conjugated to a tag via a linker is of Formula (CB-1):

CB-L¹-A-L²-TAG (CB-1), or a salt thereof, wherein:

CB is an optionally substituted cucurbituril;

TAG is a tag selected from the group consisting of polymers, therapeutic agents, targeting agents, radionuclides, fluorophores, chromophores, phosphorescent agents, dyes, chemiluminescent agents, particles, colorimetric labels, magnetic labels, haptens, biomolecules, small molecules, fatty acids, hydrocarbon chains, and diagnostic agents;

each of L¹ and L² is independently a bond, optionally substituted alkylene, or optionally substituted heteroalkylene; and A is a bond, optionally substituted heterocyclyl, or optionally substituted heteroaryl.

In certain embodiments, A is optionally substituted heteroaryl. In certain embodiments, A is optionally substituted five-membered heteroaryl. In certain embodiments, A is optionally substituted five-membered heteroaryl. A is an optionally substituted triazole moiety.

As generally defined herein, "tag" or TAG is anything that can be conjugated to the host. In certain embodiments, the tag is selected from the group consisting of polymers, therapeutic agents, targeting agents, radionuclides, fluorophores, chromophores, phosphorescent agents, dyes, chemiluminescent agents, particles, colorimetric labels, magnetic labels, haptens, biomolecules, small molecules, fatty acids, hydrocarbon chains, and diagnostic agents. In certain embodiments, the tag is a polymer. In certain embodiments, the tag is a polyboronic acid or a polyboronic ester. In certain embodiments, the tag is a polyether. In certain embodiments, the tag is a polyglycol. In certain embodiments, the tag is polyethylene glycol (PEG). In certain embodiments, the tag is PEG, and the PEG has a molecular weight <1 kDa. In certain embodiments, the PEG has a molecular weight between 1-10 kDa, inclusive. In certain embodiments, the PEG has a molecular weight of approximately 5 kDa. In certain embodiments, the PEG has a molecular weight between 5-10 kDa, inclusive. In certain embodiments, the PEG has a molecular weight of approximately 10 kDa. In certain embodiments, In certain embodiments, the PEG has a molecular weight between 10-30 kDa, inclusive. In certain embodiments, the PEG has a molecular weight of approximately 30 kDa. In certain embodiments, the PEG has a molecular weight >30 kDa. In certain embodiments, the PEG has a molecular weight under 100 kDa.

In certain embodiments, a compound comprising a host conjugated to a tag via a linker is of Formula (CB-2a) or (CB-2b):

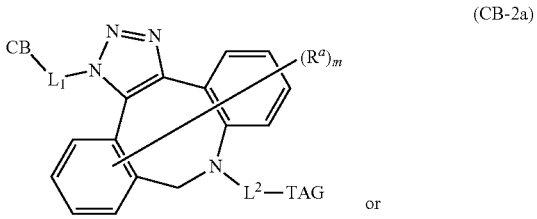

(CB-2a)

or (CB-2b)

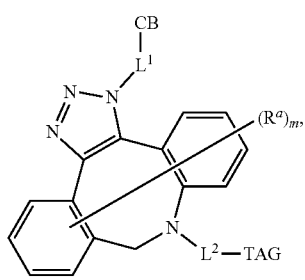

(CB-3b)

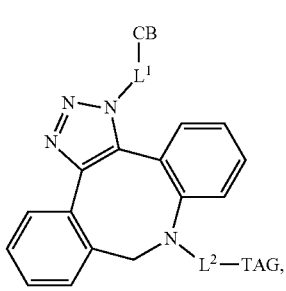

wherein:

CB is an optionally substituted cucurbituril;

TAG is a tag selected from the group consisting of polymers, therapeutic agents, targeting agents, radionuclides, fluorophores, dyes, chemiluminescent agents, particles, colorimetric labels, magnetic labels, haptens, biomolecules, small molecules, and diagnostic agents;

each of $L^1$ and $L^2$ is independently a bond, optionally substituted alkylene, or optionally substituted heteroalkylene; and Y is $CR^a$ or N;

each instance of $R^a$ is independently hydrogen, halogen, optionally substituted alkyl, optionally substituted heteroalkyl, optionally substituted alkenyl, optionally substituted alkynyl, optionally substituted acyl, optionally substituted carbocyclyl, optionally substituted heterocyclyl, optionally substituted aryl, optionally substituted heteroaryl, optionally substituted acyl, —$OR^{aa}$, —$SR^{aa}$, —$N(R^{aa})_2$, —$NO_2$, or —CN, or two $R^a$ attached to adjacent atoms are joined to form an optionally substituted carbocyclyl, optionally substituted heterocyclyl, optionally substituted aryl, optionally substituted heteroaryl ring;

each occurrence of $R^{aa}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, or a nitrogen protecting group, or two $R^{aa}$ are joined to form an optionally substituted heterocyclic or optionally substituted heteroaryl ring.

In certain embodiments, the compounds of Formulae (CB-2a) and (CB-2b) are of Formula (CB-3a) and (CB-3b), respectively:

(CB-3a)

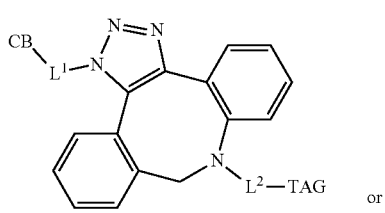

or

Or salt thereof.

In certain embodiments, $L^1$ is optionally substituted alkylene. In certain embodiments, $L^2$ is optionally substituted heteroalkylene. In certain embodiments, the compounds Formulae (CB-3a) and (CB-3b) of one of the following formulae:

(CB-4a)

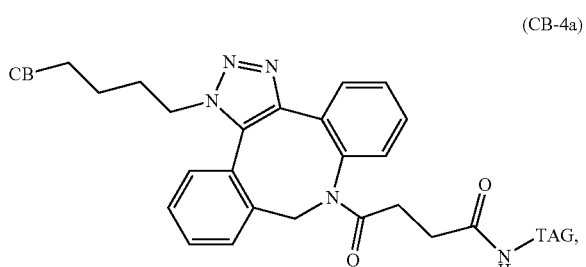

(CB-4b)

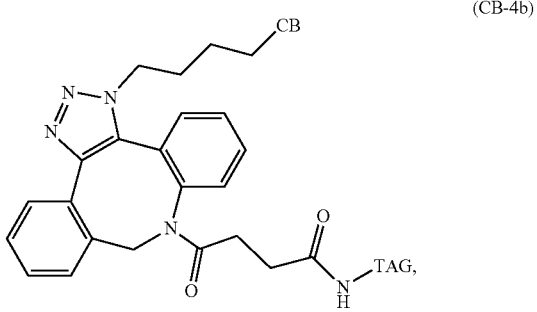

(CB-4c)

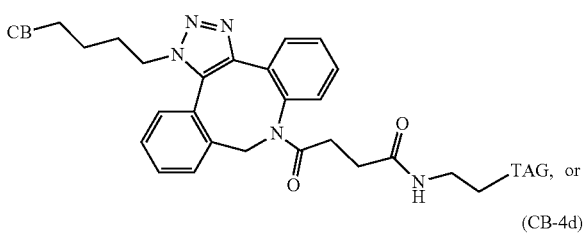

(CB-4d)

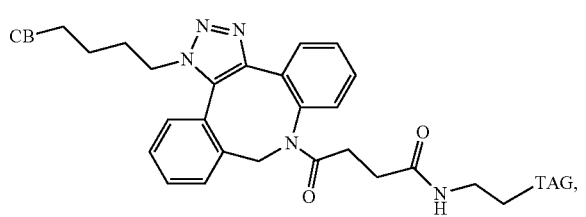

or a salt thereof.

In certain embodiments, the host conjugated to a tag via a linker is of the Formula (PEG-T-CB[7]):

(PEG-T-CB[7])

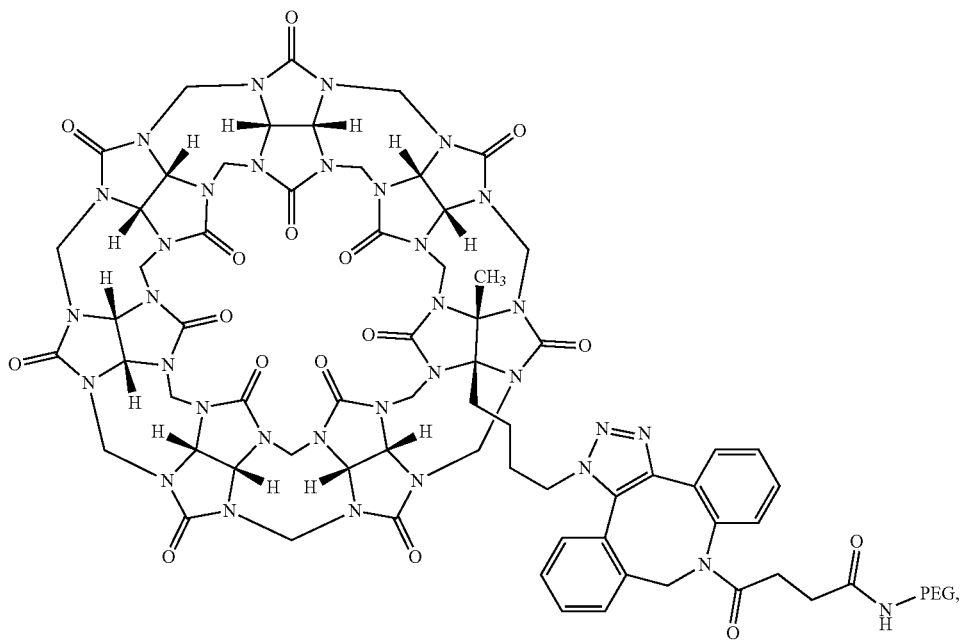

or a salt thereof.

In certain embodiments, the host conjugated to a tag via a linker is of the Formula (CB-5):

(CB-5)

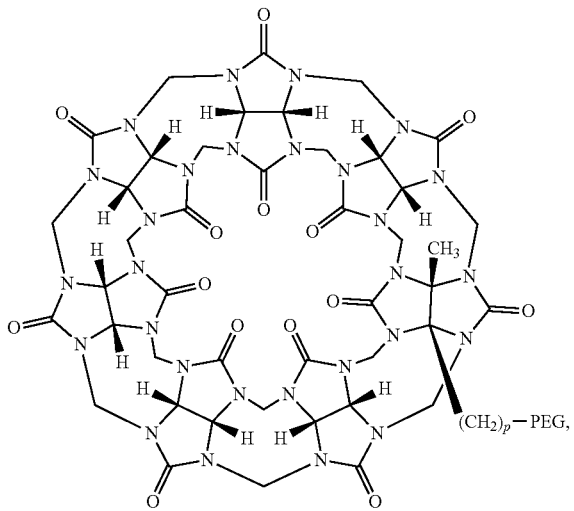

or salt thereof, wherein p is an integer between 0-20, inclusive.

Methods

The present invention also provides methods of preparing supramolecular complexes described herein, as well as compounds that are useful in preparing the supramolecular complexes.

Methods for Preparing Supramolecular Complexes

Provided herein are methods for preparing agents associated with tags, wherein the agent is specifically bound to a host via non-covalent interactions, and wherein the host is conjugated to the tag (referred to herein as "supramolecular complexes"). A typical method for preparing a supramolecular conjugate of the present invention comprises:

contacting an agent with a host;

wherein the host is conjugated to the tag; and wherein the tag is selected from the group consisting of polymers, therapeutic agents, targeting agents, radionuclides, fluorophores, chromophores, phosphorescent agents, dyes, chemiluminescent agents, particles, colorimetric labels, magnetic labels, haptens, biomolecules, small molecules, and diagnostic agents.

It is to be understood that the agent that is associated with a tag can be anything. In certain embodiments, the agent that is associated with a tag is selected from the group consisting of biomolecules, small molecule drugs, imaging agents, and diagnostic agents. In certain embodiments, the agent is a small molecule. In certain embodiments, the agent is a therapeutic small molecule. In certain embodiments, the agent is a biomolecule. In certain embodiments, the agent is a therapeutic biomolecule. In certain embodiments, the agent is a biomolecule selected from the group consisting of proteins, peptides, nucleic acids, polysaccharides, and lipids. In certain embodiments, the agent is a peptide. In certain embodiments, the agent is a protein. In certain embodiments, the agent is an enzyme. In certain embodiments, the agent is an antibody or antibody fragment. In certain embodiments, the agent is a monoclonal antibody. In certain embodiments, the agent is a polyclonal antibody. In certain embodiments, the agent is an antibody for human CD20. Examples of anti-CD20 antibodies include, but are not limited to, rituximab, obinutuzumab, Ibritumomab tiuxetan, tositumomab, Ofatumumab (Genmab), obinutuzumab (Gazyva), Ocaratuzumab, Ocrelizumab, and IMMU-106 (veltuzumab). In certain embodiments, the agent is an anticancer antibody (e.g., trastuzumab, rituximab). In certain embodiments, the agent is a polysaccharide. In certain embodiments, the agent is a lipid. In certain embodiments, the agent is a nucleic acid. (e.g., DNA, RNA, and hybrids thereof). In certain embodiments, the agent is a protein. In certain embodiments, the agent is a therapeutic protein. In certain embodiments, the agent is a modified protein. In certain embodiments, the agent is a native or wild-type protein. In certain embodiments, the agent is GLP-1 or an analogue thereof. In certain embodiments, the agent is an interferon. In certain embodiments, the agent is a growth factor (e.g., BMP-2, VEGF, FGF-2, PDGF). In certain embodiments, the agent is a growth hormone. In certain embodiments, the agent is glucagon. In certain embodiments, the agent is insulin. In certain embodiments, the agent is a derivative of insulin. In certain embodiments, the agent is native or wild type insulin.

As described herein, method for preparing supramolecular complexes of the present invention comprises contacting an agent with a host. In certain embodiments, the host is a macrocycle. In certain embodiments, the macrocyclic host is selected from the group consisting of cucurbiturils, cyclodextrins, calixarenes, pillararenes, porphyrins, metallacrowns, crown ethers, cyclotriveratrylenes, cryptophanes, cyclophanes, and carcerands. In certain embodiments, the macrocyclic host is a cyclophane. In certain embodiments, the macrocyclic host is a cyclophane comprising paraquat moieties. In certain embodiments, the host is cyclobis(paraquat-p-phenylene). In certain embodiments, the macrocyclic host is a cucurbituril, wherein cucurbituril is as defined herein. In certain embodiments, the host is an optionally substituted acyclic cucurbituril. See, e.g., Isaacs et al. *Nat. Chem.* 2012, 4, 503-510. In certain embodiments, the macrocyclic host is an optionally substituted cucurbituril. In certain embodiments, the macrocyclic host is a substituted cucurbituril. In certain embodiments, the host is an optionally substituted cucurbit[n]uril (CB[n]), wherein n is an integer between 5-10, inclusive. In certain embodiments, n is 5. In certain embodiments, n is 6. In certain embodiments, n is 7. In certain embodiments, n is 8. In certain embodiments, n is 9. In certain embodiments, n is 10. In certain embodiments, n is 7, and the host is optionally substituted cucurbit[7]uril (CB[7]).

As described herein, the host is conjugated to a tag. In certain embodiments, the tag is selected from the group consisting of polymers, therapeutic agents, targeting agents, radionuclides, fluorophores, chromophores, phosphorescent agents, dyes, chemiluminescent agents, particles, colorimetric labels, magnetic labels, haptens, biomolecules, small molecules, excipients, and diagnostic agents. In certain embodiments, the tag is a polymer. In certain embodiments, the tag is an excipient (e.g., a pharmaceutically acceptable excipient). In certain embodiments, the tag is a polyboronic acid or a polyboronic ester. In certain embodiments, the tag is a polyether. In certain embodiments, the tag is a polyglycol. In certain embodiments, the tag is polyethylene glycol (PEG).

As described herein, the method for preparing supramolecular complexes comprises contacting an agent (e.g., biomolecule, small molecule, imaging agent, or diagnostic agent) with a host conjugated to a tag. In certain embodiments, the method comprises contacting a biomolecule with a host conjugated to a tag. In certain embodiments, the method comprises contacting a protein with a host conjugated to a tag. In certain embodiments, the method comprises contacting a therapeutic protein with a host conjugated to a tag. In certain embodiments, the method comprises contacting insulin with a host conjugated to a tag.

In particular embodiments, the method comprises contacting a biomolecule with a cucurbituril conjugated to a tag. In certain embodiments, the method comprises contacting a biomolecule with an optionally substituted CB[7] conjugated to a tag. In certain embodiments, the method comprises contacting a biomolecule with a host conjugated to a polymer. In certain embodiments, the method comprises contacting a biomolecule with a host conjugated to polyethylene glycol (PEG). In certain embodiments, the method comprises contacting a biomolecule with a cucurbituril conjugated to a polymer. In certain embodiments, the method comprises contacting a biomolecule with CB[7] conjugated to PEG. In certain embodiments, the method comprises contacting a biomolecule with a compound of any one of Formulae (CB-1), (CB-2a), (CB-2b), (CB-3a), (CB-3b), (CB-4a), (CB-4b), (CB-4c), (CB-4d), (CB-5) or (PEG-T-CB[7]).

In particular embodiments, the method comprises contacting insulin with an optionally substituted cucurbituril conjugated to a polymer. In particular embodiments, the method comprises contacting insulin with an optionally substituted CB[7] conjugated to PEG. In particular embodiments, the method comprises contacting insulin with a compound of any one of Formulae (CB-1), (CB-2a), (CB-2b), (CB-3a), (CB-3b), (CB-4a), (CB-4b), (CB-4c), (CB-4d), (CB-5) or (PEG-T-CB[7]).

In certain embodiments, the step of contacting an agent with a host conjugated to a tag is performed in vitro. In certain embodiments, the step of contacting an agent with a host conjugated to a tag is performed in vivo. In certain embodiments, the step of contacting is performed in a solvent. In certain embodiments, the step of contacting is performed in an organic solvent. In certain embodiments, the step of contacting is performed in an inorganic solvent. In certain embodiments, the solvent is water. In certain embodiments, the step of contacting is performed at ambient temperature. In certain embodiments, the step of contacting is performed at a temperature above ambient temperature. In certain embodiments, an excess (i.e., superstoichiometric amount) of host-tag conjugate relative to the agent is used. In certain embodiments, an excess of the agent relative to the host-tag conjugate is used.

Methods for Preparing Host-Tag Conjugates

As described herein, host molecules that are conjugated to tags (also referred to herein as "host-tag conjugates") are compounds that are useful in preparing supramolecular conjugates. The present invention provides methods for preparing host-tag conjugates.

It should be understood that any covalent bond-forming reaction can be used to conjugate a tag to a host in order provide a host-tag conjugate of the present invention. Exemplary reactions include, but are not limited to, alkylation reactions, metathesis reactions, addition reactions, substitution reactions, cycloaddition reactions, etc. In certain embodiments, the reaction used to conjugate the host to the tag is a cycloaddition reaction. In certain embodiments, the cycloaddition is a [4+2] cycloaddition. In certain embodiments, the cycloaddition is a 1,3-dipolar cycloaddition. In certain embodiments, the reaction is an azide-alkyne cycloaddition (i.e., Huisgen cycloaddition). In certain embodiments, the cycloaddition is performed in the presence of a catalyst. In certain embodiments, the catalyst is a copper catalyst. In certain embodiments, the cycloaddition reaction is a copper-free reaction. In certain embodiments, the azide-alkyne cycloaddition involved a cyclic alkyne and is strain-promoted.

In certain embodiments, the reaction used to conjugate the host to the tag is a "click chemistry" reaction (e.g., the Huisgen alkyne-azide cycloaddition). It is to be understood that any "click chemistry" reaction known in the art can be used to this end. Click chemistry is a chemical approach introduced by Sharpless in 2001 and describes chemistry tailored to generate substances quickly and reliably by joining small units together. See, e.g., Kolb, Finn and Sharpless *Angewandte Chemie International Edition* (2001) 40: 2004-2021; Evans, *Australian Journal of Chemistry* (2007) 60: 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition); and Diels-Alder reactions (e.g., tetrazine[4+2] cycloaddition).

In certain embodiments, the method of preparing a host-tag conjugate comprises contacting a cucurbituril derivative comprising a first click chemistry handle with a tag comprising a second click chemistry handle. In certain embodiments, the method comprises contacting a cucurbituril derivative comprising an azide moiety with a tag comprising an alkyne moiety. In certain embodiments, the alkyne is a strained alkyne. In certain embodiments, the method comprises contacting a cucurbituril derivative comprising an alkyne moiety with a tag comprising an azide moiety. In certain embodiments, the alkyne moiety is a strained alkyne.

In certain embodiments, the method comprises coupling a compound of Formula (Az-1):

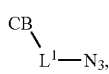
(Az-1)

or salt thereof, with a compound of Formula (Ak-1):

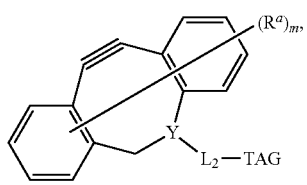
(Ak-1)

or salt thereof, to yield a compound of Formula (CB-2a) or (CB-2b):

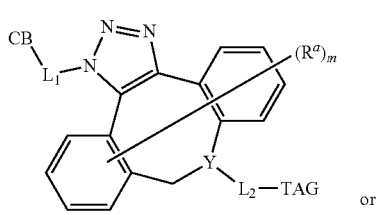
(CB-2a)

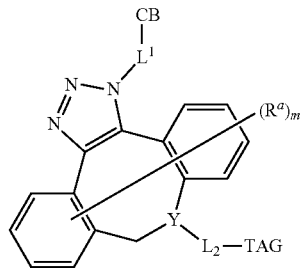
(CB-2b)

or salt thereof, wherein:

CB is an optionally substituted cucurbituril;

TAG is a tag selected from the group consisting of polymers, therapeutic agents, targeting agents, radionuclides, fluorophores, dyes, chemiluminescent agents, particles, colorimetric labels, magnetic labels, haptens, biomolecules, fatty acids, hydrocarbon chains, small molecules, excipients, and diagnostic agents;

each of $L^1$ and $L^2$ is independently a bond, optionally substituted alkylene or heteroalkylene;

m is an integer from 0-10, inclusive;

each instance of $R^a$ is independently hydrogen, halogen, optionally substituted alkyl, optionally substituted heteroalkyl, optionally substituted alkenyl, optionally substituted alkynyl, optionally substituted acyl, optionally substituted carbocyclyl, optionally substituted heterocyclyl, optionally substituted aryl, optionally substituted heteroaryl, optionally substituted acyl, —$OR^{aa}$, —$SR^{aa}$, —$N(R^{aa})_2$, —$NO_2$, or —CN, or two $R^a$ attached to adjacent atoms are joined to form an optionally substituted carbocyclyl, optionally substituted heterocyclyl, optionally substituted aryl, optionally substituted heteroaryl ring; and each occurrence of $R^{aa}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, or a nitrogen protecting group, or two $R^{aa}$ are joined to form an optionally substituted heterocyclic or optionally substituted heteroaryl ring.

In certain embodiments, CB is optionally substituted cucurbit[7]uril (CB[7]). In certain embodiments, CB is substituted cucurbit[7]uril (CB[7]). In certain embodiments, CB is unsubstituted cucurbit[7]uril (CB[7]).

In certain embodiments, the method comprises contacting a compound of Formula (Az-1), or salt thereof, with a compound of one of the following formulae:

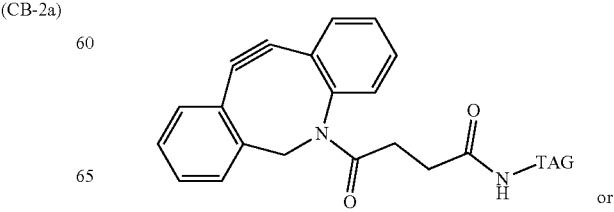

or

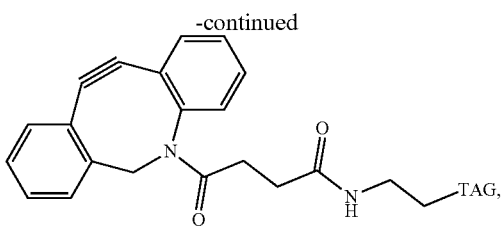

or a salt thereof.

In particular embodiments, the compound of Formula (Az-1) is of Formula (Az-2):

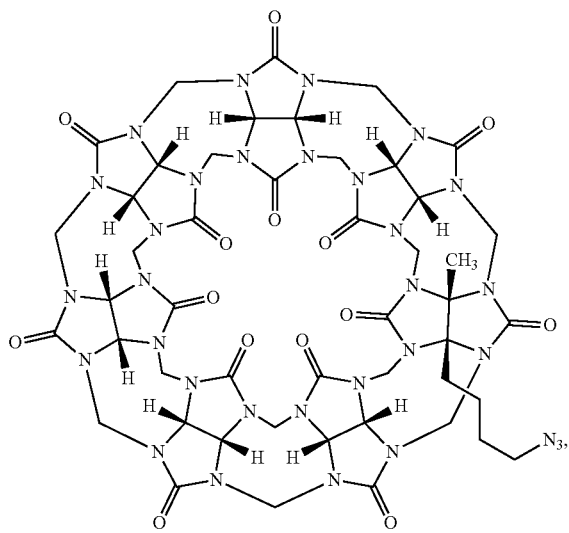

(Az-2)

or salt thereof.

In certain embodiments, the tag with a click chemistry handle is of Formula (PEG-DBCO):

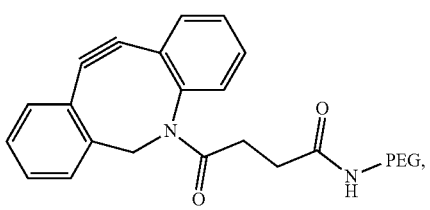

(PEG-DBCO)

or salt thereof.

Pharmaceutical Compositions, Kits, and Administration

The present disclosure provides pharmaceutical compositions comprising a supramolecular complex or acceptable salt thereof, and optionally a pharmaceutically acceptable excipient. In certain embodiments, the pharmaceutical composition described herein comprises any supramolecular complex described herein or a pharmaceutically acceptable salt thereof, and a pharmaceutically acceptable excipient.

In certain embodiments, the supramolecular complex described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a metabolic disorder in a subject in need thereof. In certain embodiments, the effective amount is an amount effective for preventing a metabolic disorder in a subject in need thereof. In certain embodiments, the effective amount is an amount effective for treating a diabetic condition in a subject in need thereof. In certain embodiments, the effective amount is an amount effective for preventing a diabetic condition in a subject in need thereof. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating cancer (e.g., a lymphoma or leukemia) in a subject in need thereof. In certain embodiments, the effective amount is an amount effective for preventing a recurrence of cancer (e.g., a lymphoma or leukemia) in a subject in need thereof.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the idagent, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof. In certain embodiments of the invention, one or more of these surface active agents/emulsifiers is the tag conjugated to the host in the supramolecular complexes described herein. In certain embodiments of the invention, one or more of these surface active agents/emulsifiers is the tag conjugated to the host in the host-tag conjugates described herein.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid. Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the complexes described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U. S. P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the complexes described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Complexes provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The complexes and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a complex required to achieve an effective amount will vary from subject to subject, depending, for example, on species, age, and general condition of a subject, severity of the side effects or disorder, idagent of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A complex or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The supramolecular complex or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Also encompassed by the disclosure are kits (e.g., pharmaceutical packs). The kits provided may comprise a pharmaceutical composition or supramolecular complex described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a supramolecular complex or pharmaceutical composition described herein. In certain embodiments, the kits are useful for treating a disease (e.g., proliferative disease, hematological disease, neurological disease, painful condition, psychiatric disorder, or metabolic disorder) in a subject in need thereof. In certain embodiments, the kits are useful for preventing a disease (e.g., proliferative disease, hematological disease, neurological disease, painful condition, psychiatric disorder, or metabolic disorder) in a subject in need thereof. In certain embodiments, the kits are useful for reducing the risk of developing a disease (e.g., proliferative disease, hematological disease, neurological disease, painful condition, psychiatric disorder, or metabolic disorder) in a subject in need thereof. In certain embodiments, the kits are useful for inhibiting the activity (e.g., aberrant activity, such as increased activity) of a protein kinase in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, hematological disease, neurological disease, painful condition, psychiatric disorder, or metabolic disorder) in a subject in need thereof. In certain embodiments, the kits and instructions provide for preventing a disease (e.g., proliferative disease, hematological disease, neurological disease, painful condition, psychiatric disorder, or metabolic disorder) in a subject in need thereof. In certain embodiments, the kits and instructions provide for reducing the risk of developing a disease (e.g., proliferative disease, hematological disease, neurological disease, painful condition, psychiatric disorder, or metabolic disorder) in a subject in need thereof. In certain embodiments, the kits and instructions provide for inhibiting the activity (e.g., aberrant activity, such as increased activity) of a protein kinase in a subject or cell. A kit described herein may include one or more additional pharmaceutical agents described herein as a separate composition.

Methods of Treatment and Use

The present invention also provides methods for the treatment or prevention of diseases including, but not limited to, proliferative diseases, diseases associated with angiogenesis, genetic disorders, inflammatory diseases, cardiovascular diseases, hepatic diseases, splenic diseases, gastrointestinal diseases, pulmonary diseases, painful conditions, hematological diseases, neurological diseases, psychiatric disorders, autoimmune diseases, infectious diseases, neurological diseases, metabolic disease, or endocrine diseases. In certain embodiments, a method of treating a disease in a subject in need thereof comprises administering to the subject a therapeutically effective amount of a supramolecular complex described herein, or a salt thereof.

In certain embodiments, the disease is a metabolic disease. In certain embodiments, the disease is diabetes. In certain embodiments, the disease is Type II diabetes.

In certain embodiments, the disease is a proliferative disease. In certain embodiments, the disease is cancer. In certain embodiments, the disease is a hematological cancer. In certain embodiments, the disease is a lymphoma, leukemia, or myeloma. In certain embodiments, the disease is lymphoma. In certain embodiments, the disease is leukemia. In certain embodiments, the disease is chronic lymphocytic leukemia.

All types of autoimmune and inflammatory diseases disclosed herein or known in the art are contemplated as being treatable using the inventive compositions and methods described herein.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

In certain embodiments, the methods described herein include administering to a subject or contacting a biological sample with an effective amount of a supramolecular complex described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the methods described herein include administering to a subject or contacting a biological sample with an effective amount of a supramolecular complex described herein, or a pharmaceutically acceptable salt thereof, or a pharmaceutical composition thereof. In certain embodiments, the supramolecular complex is contacted with a biological sample. In certain embodiments, the supramolecular complex is administered to a subject. In certain embodiments, the supramolecular is administered in combination with one or more additional pharmaceutical agents.

The present invention also provides uses of supramolecular complexes described herein for the treatment of diseases described herein. The present invention also provides uses of supramolecular complexes described herein for the preparation of medicaments for treating diseases described herein.

EXAMPLES

In order that the invention described herein may be more fully understood, the following examples are set forth. The examples described in this application are offered to illustrate the supramolecular complexes and methods provided herein and are not to be construed in any way as limiting their scope.

PEGylation of Insulin

Insulin is one of the most widely used biopharmaceuticals, and is a key component in the treatment of both type-I and type-II diabetes. See, e.g., Patterson et al. *Lancet* 2009, 373(9680): 2027-2033; Zimmet et al. *Nature* 2001, 414 (6865): 782-787; Wild et al. *Diabetes Care* 2004, 27(5): 1047-1053. The protein is known to have limited solution stability, even in refrigerated storage, and is prone to the formation of amyloid fibrils. See, e.g., Jimenez et al. *Proc Natl Acad Sci USA* 2002, 99(14): 9196-9201; Sluzky et al. *Proc Natl Acad Sci USA* 1991, 88(21): 9377-9381; Fisher et al. *The Journal of pharmacy and pharmacology* 1981, 33(4): 203-206. Insulin used clinically is formulated with a number of excipients to maximize its shelf life; most available formulations are stable for up to one month when refrigerated. See, e.g., Grajower et al. *Diabetes Care* 2003, 26(9): 2665-2669. However, the incorporation of insulin into pumps or implantable delivery devices, along with variable handling from patients, introduces complications that could reduce protein stability, leading to limited therapeutic efficacy. See, e.g., Lougheed et al. *Diabetologia* 1980, 19(1): 1-9; Renard et al. *Current opinion in pharmacology* 2002, 2(6): 708-716. Extensive work has been done to achieve site-specific PEGylation of insulin to control both its physical stability and pharmacological properties. See, e.g., Hinds et al. *Adv Drug Deliv Rev* 2002, 54(4): 505-530; Hinds et al. *Bioconjug Chem* 2000, 11(2): 195-201; Uchio et al. *Adv Drug Deliv Rev* 1999, 35(2-3): 289-306. Specifically, PEGylation has been shown to reduce insulin aggregation and fibril formation, reduce immunogenicity and allergenicity, and increase serum circulation half-life. Alternatively, a number of insulin variants have been developed to reduce aggregation or promote long-lasting activity, as well as other approaches to improve stability by supramolecular zinc-stapling, and approaches to facilitate glucose-responsive bioavailability. See, e.g., Hirsch I B. *N Engl J Med* 2005, 352(2): 174-183; Owens D R. *Nat Rev Drug Discov* 2002, 1(7): 529-540; Phillips et al. *J Biol Chem* 2010, 285(16): 11755-11759; Chou et al. *Proc Natl Acad Sci USA* 2015, 112(8): 2401-2406.

We developed a strategy to utilize a CB[7] host-modified with a single PEG chain for supramolecular PEGylation of native insulin via host-guest complexation. Supramolecular PEGylation of native insulin enhances stability of the protein by preventing aggregation and also provides longer lasting pharmacological activity in a diabetic mouse model. This strategy could be employed as an excipient-only approach to provide both enhanced stability and long-lasting activity of therapeutic proteins through supramolecular complex formation.

Though CB[7] exhibits exceptional binding affinities for a broad range of guest molecules it has been significantly more difficult to functionalize or conjugate than other classes of cyclic host molecules. See, e.g., Rekharsky et al. *Proc Natl Acad Sci USA* 2007, 104(52): 20737-20742; Moghaddam et al. *J Am Chem Soc* 2011, 133: 3570-3581; Cao et al. *Angewandte Chemie* 2014, 53(4): 988-993; Kim et al. *Chem Soc Rev* 2007, 36(2): 267-279; Lee et al. *Acc Chem Res* 2003, 36(8): 621-630. Two synthetic routes have recently been described to prepare monofunctionalized CB[7] derivatives with synthetically useful handles. See, e.g., Vinciguerra et al. *Journal of the American Chemical Society* 2012, 134(31): 13133-13140; Ahn et al. *Angewandte Chemie* 2013, 52(11): 3140-3144; Cao et al. *Angewandte Chemie* 2013, 52(46): 12033-12037. Using the Isaacs group methods, CB[7]-$N_3$ was synthesized to prepare supramolecular PEG conjugates by of copper-free "click" chemistry. Dibenzocyclooctyne (DBCO)-modified poly(ethylene glycol) (PEG-DBCO) polymers of varying molecular weights ($M_n$=5 kDa, 10 kDa, and 30 kDa) were reacted with CB[7]-$N_3$ to yield PEG-T-CB[7], connected via a triazole linkage (FIG. 1A). PEG chains of three different molecular weights were selected to enable a study of the effect of PEG chain length on the stability and pharmacological activity of native insulin following supramolecular PEGylation.

Figure 2A:
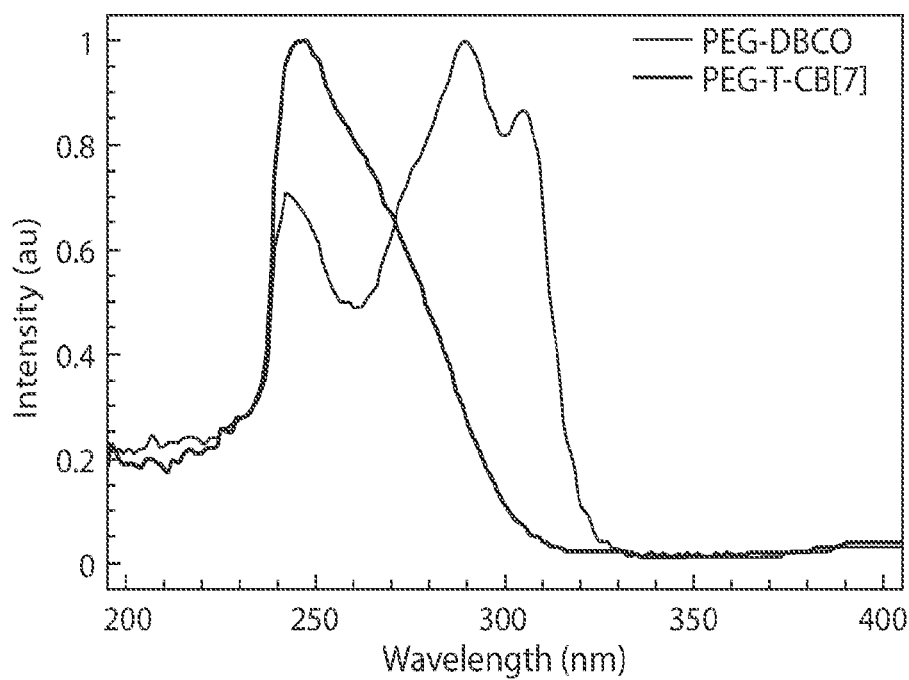
FIGS. 2A-2D. Characterization of PEG-T-CB[7] conjugates.
Figure 2B:
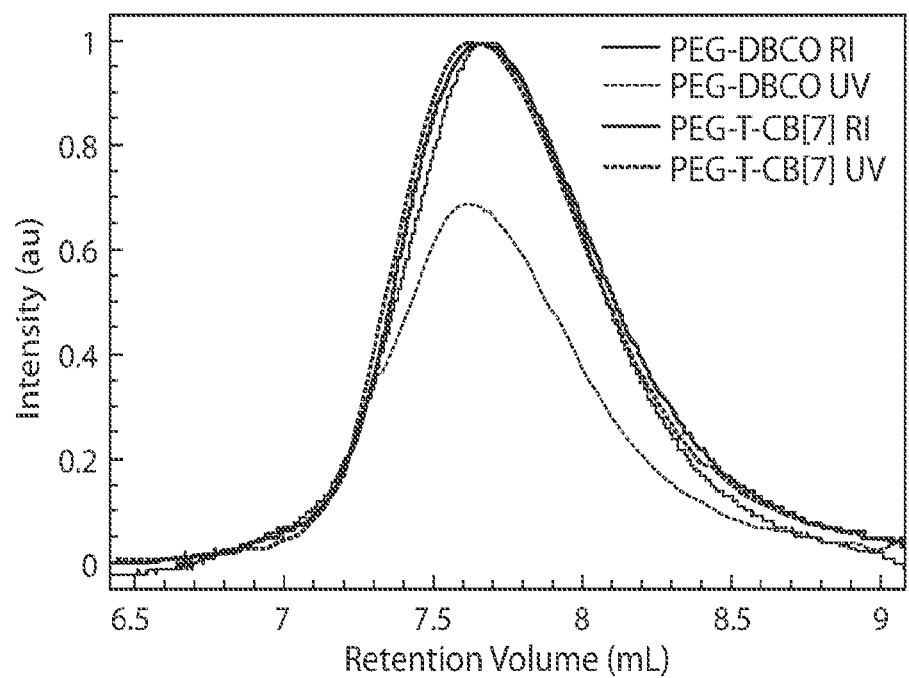
Figure 2C:
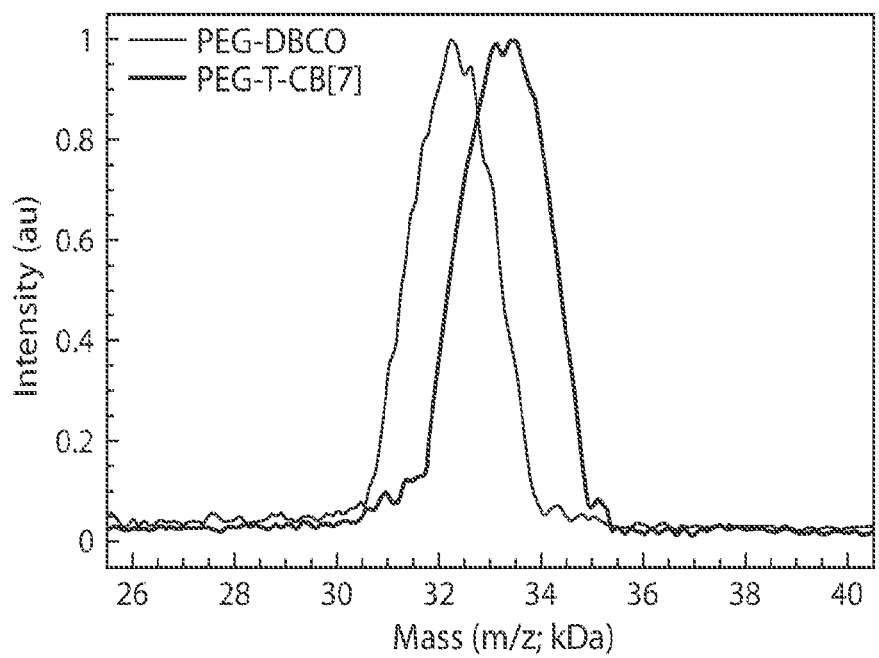

Gel permeation chromatography (GPC) with UV/visible detection (FIGS. 2A and 2B) was performed to verify the reaction between PEG-DBCO and CB[7]-$N_3$ and characterize the PEG-T-CB[7]. The UV/visible spectrum upon GPC elution demonstrates a characteristic change in absorbance from the PEG-DBCO starting material to PEG-T-CB[7] resulting from triazole formation, with a blue-shift in $\lambda_{max}$ from 290 nm to 248 nm. Moreover, these DBCO and triazole signatures appear concurrent with elution of the polymeric backbone, as indicated by the refractive index trace. Additionally, matrix-assisted laser desorption ionization (MALDI) mass spectrometry demonstrates a characteristic increase in molecular weight for PEG-T-CB[7] relative to the PEG-DBCO starting material (FIG. 2C). The shift in the observed peak of the MALDI-MS spectrum following reaction of the 30 kDa PEG-DBCO with CB[7]-$N_3$ corresponds to a mass increase of approximately 1200 Da, consistent with addition of a single CB[7]-$N_3$ moiety.

Figure 2D:
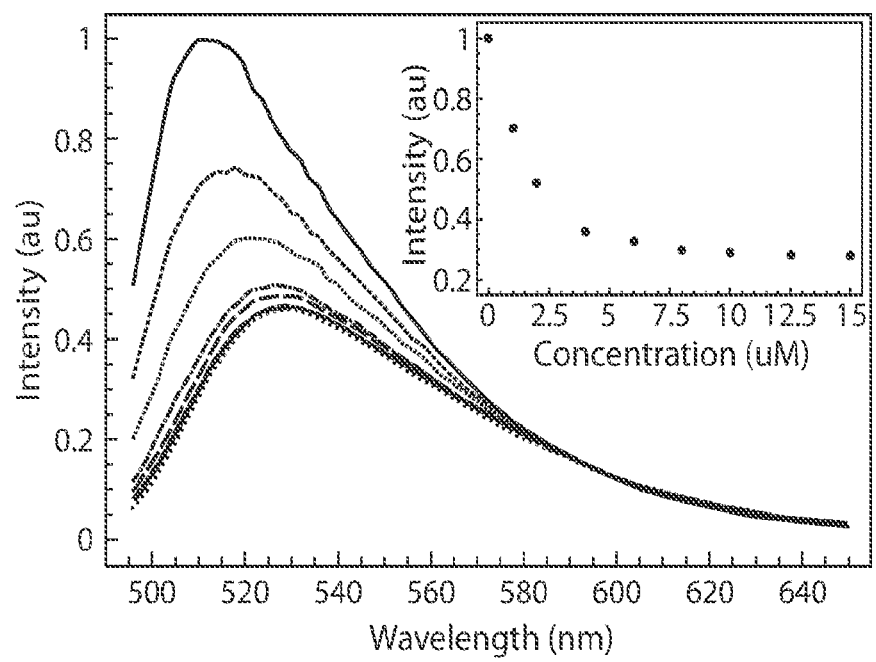
Figure 7:
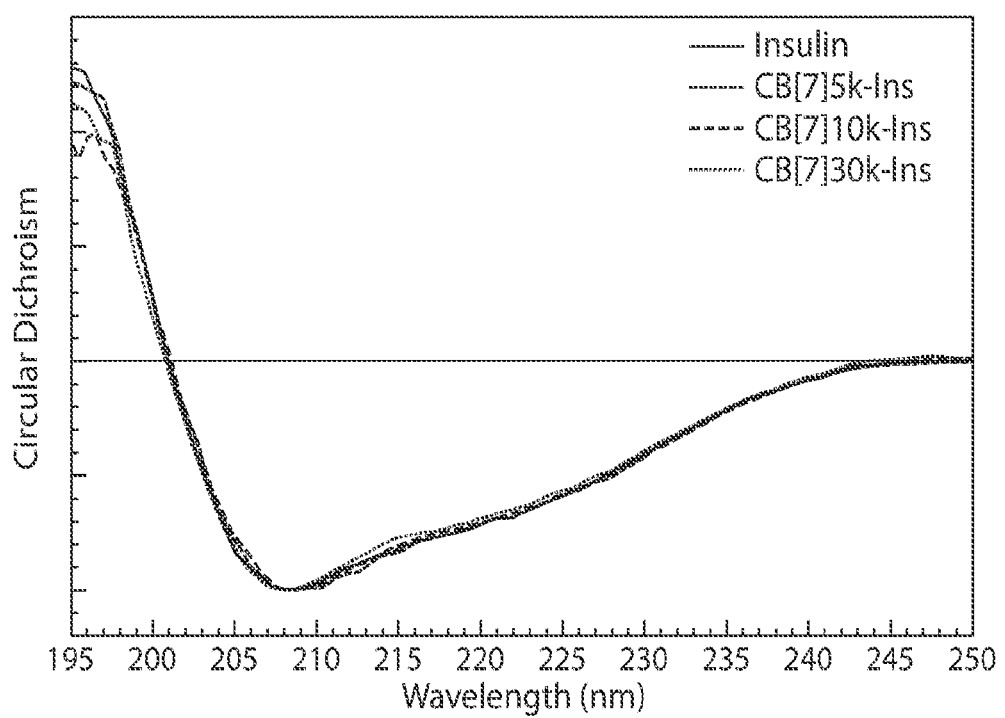
FIG. 7. Near-ultraviolet circular dichroism spectra of insulin or insulin formulated with CB[7]-PEG conjugates. Spectra demonstrate no changes in insulin circular dichroism signal, with a characteristic α-helical signature.

As mentioned above, CB[7] has been shown to bind to the B1 phenylalanine residue of native insulin. To confirm binding of PEG-T-CB[7] to native insulin, a competitive binding assay was performed using acridine orange (AO) (FIG. 2D). In this assay, the fluorescent emission spectrum of AO is collected. The fluorescence intensity of AO increases when in complex with CB[7] relative to its emission when free in solution. As insulin is added, the CB[7]*AO complex dissociates as a result of stronger binding affinity of the B1 Phenylalanine residue to the CB[7], resulting in a reduction to the measured fluorescence intensity of AO. When fitting this data to a one-site competitive binding model, no significant difference in the binding constant toward insulin was observed in comparing unmodified authentic CB[7] to PEG-T-CB[7] (CB[7], $K_D$=2.3±0.2 µM vs. $PEG_{30k}$-T-CB[7], $K_D$=2.1±0.3 µM). Furthermore, binding to insulin by PEG-T-CB[7] does not alter the secondary structure of native insulin, as measured by circular dichroism spectroscopy (FIG. 7), suggesting no negative effect of supramolecular PEGylation on the secondary structure of the protein.

Figure 3A:
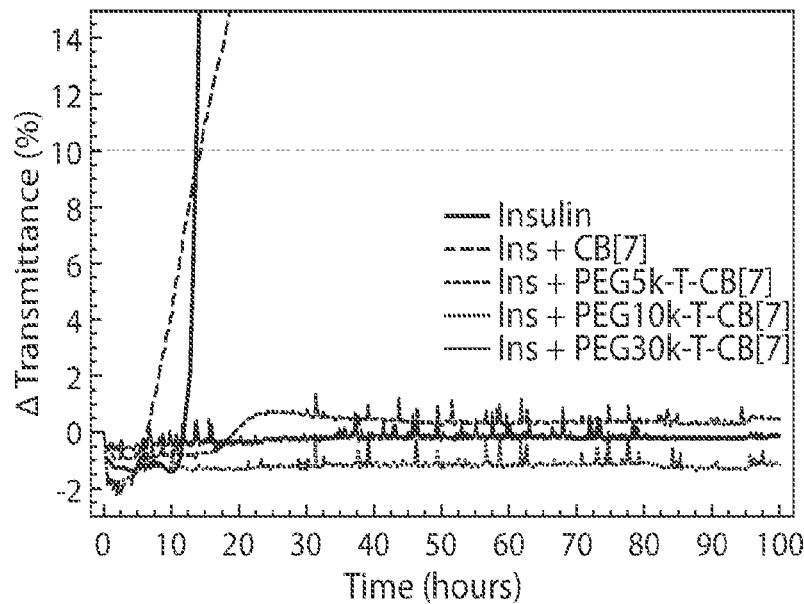
FIGS. 3A-3B. Stabilization of native insulin with PEG-T-CB[7] conjugates.
Figure 3B:
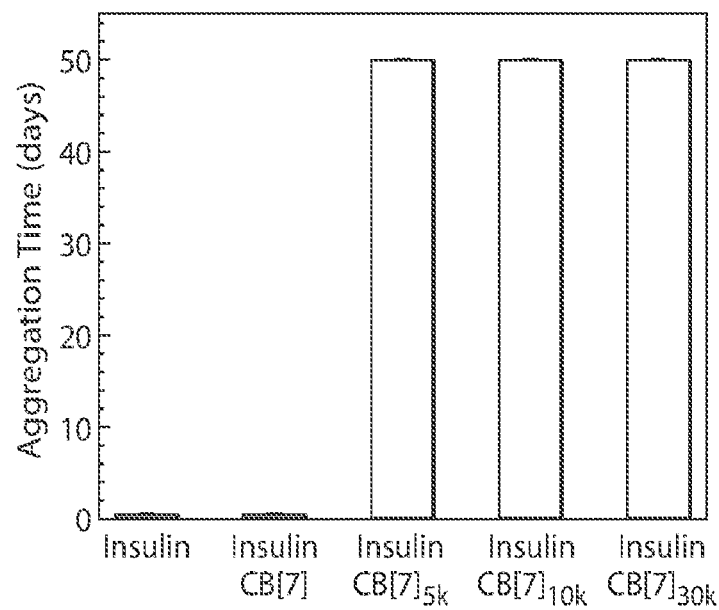
Figure 8:
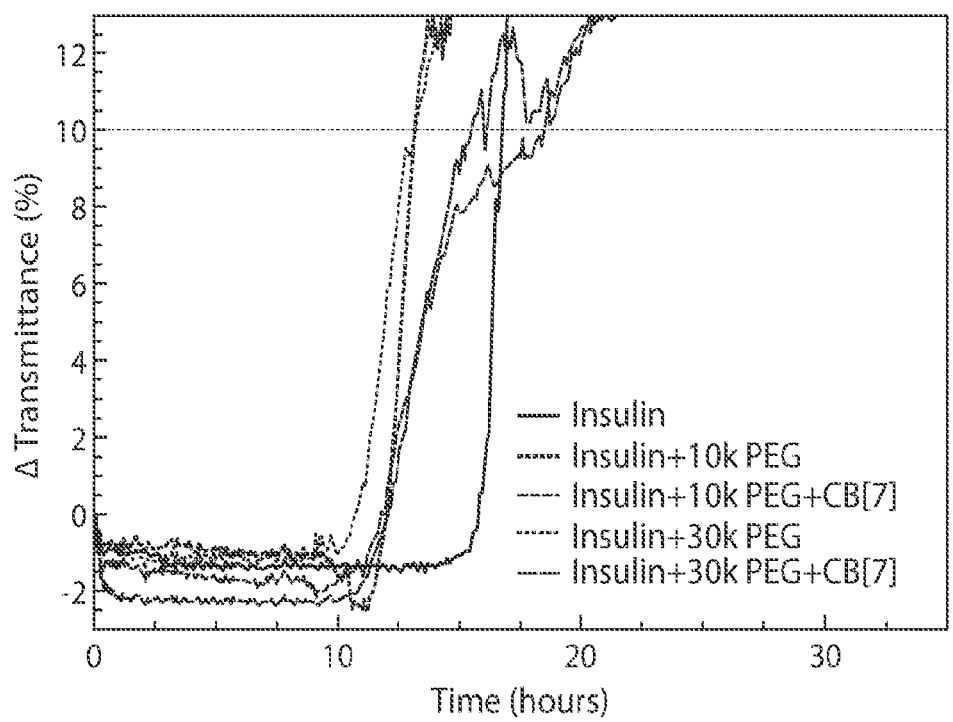
FIG. 8. Kinetic studies of the aggregation of various formulations of native insulin (1 mg/ml) at pH 7.4 and 37° C. in PBS with continuous agitation for insulin alone, or formulated with PEG (1 equivalent; $M_n$=10 kDa or 30 kDa), with and without unmodified CB[7] (1 equivalent).
Figure 9A:
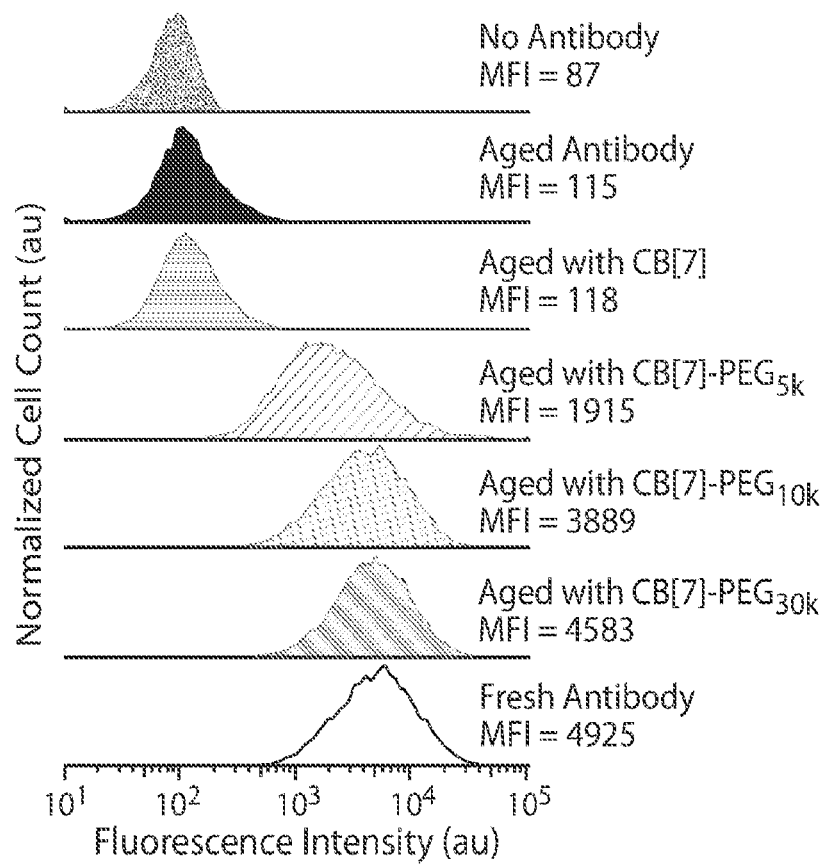
FIGS. 9A-9C. Validation of stability with other biopharmaceuticals.
Figure 9B:
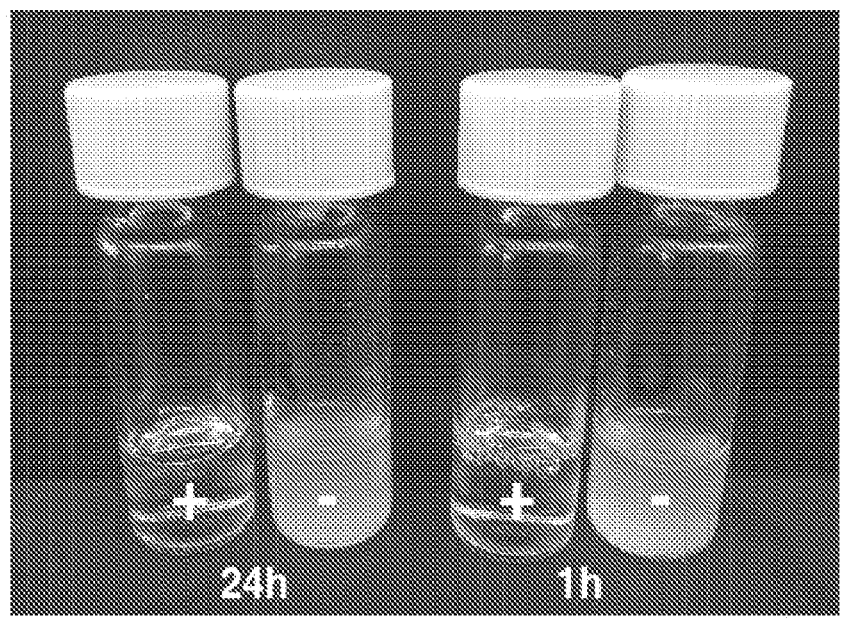
Figure 9C:
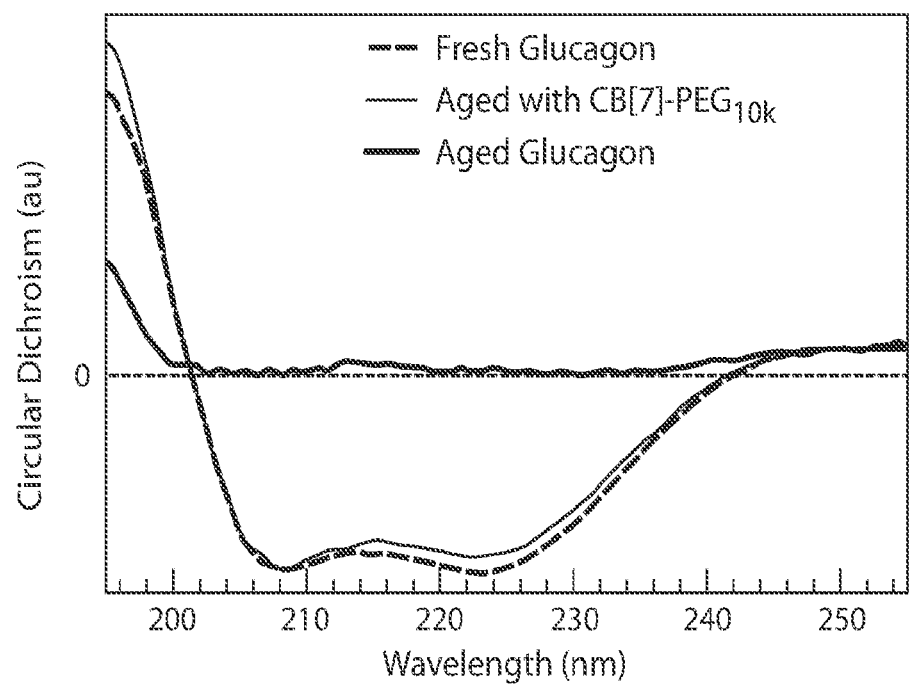

Insulin is well known to form fibrillar aggregates in physiologic conditions. To determine whether PEG-T-CB[7] can stabilize insulin and prevent its aggregation, assays were performed in physiologic salt concentrations at pH 7.4 and 37° C. with continuous agitation to determine the kinetics of insulin aggregation in a solution of 1 mg/mL protein (FIG. 3A). Specifically, transmittance was measured at 540 nm, a wavelength where both insulin and the PEG-T-CB[7] have negligible absorbance in order to detect the formation of aggregates, which scatter light, in solution over time. Defining aggregation time ($t_A$) as the time after which a 10% reduction in transmittance is observed, native insulin aggregates after 13.6±0.2 h of agitation and insulin formulated with unmodified CB[7] displays an aggregation time of 14.2±0.4 h. Meanwhile, insulin formulated with all molecular weights of PEG-T-CB[7] did not aggregate in 100 hours of kinetic study. After the initial 100 h study, data were collected once daily to determine the duration of stability for each PEG-T-CB[7]/insulin formulation (FIG. 3B). At the 50 day endpoint of these studies, formulation of insulin with $PEG_{5k}$-T-CB[7], $PEG_{10k}$-T-CB[7], and $PEG_{30k}$-T-CB[7] remained stable and were not aggregated. Serial monitoring for 100 days indicated no insulin aggregation in CB[7]-PEG formulated groups, and furthermore, in vitro activity assays at the study endpoint demonstrated preserved insulin signaling for CB[7]-PEG formulations (FIG. 4B). As a control, the addition of PEG polymers of comparable molecular weights alone and in combination with unmodified CB[7] was not found to prolong insulin stability (FIG. 8), highlighting the importance of supramolecular PEGylation with PEG-T-CB[7] in enhancing the stability of native insulin.

Here we have demonstrated that supramolecular PEGylation using PEG-T-CB[7] conjugates significantly inhibits insulin aggregation. Since the process of insulin aggregation is initiated by a stochastic nucleation event and is dependent on the specific materials and conditions used, it can be challenging to directly compare these findings to others reported previously. Aggregation of insulin is most commonly studied using thioflavin T (ThT). See, e.g., Krebs et al. *Journal of structural biology* 2005, 149(1): 30-37. In order to avoid confounding effects on account of competitive binding of ThT to CB [7], aggregation was monitored here using transmittance. Nonetheless, the observed time for aggregation of native insulin in our studies is consistent with those from a number of published reports. See, e.g., Dutta Choudhury et al. *J Phys Chem B* 2009, 113(7): 1891-1898; Lee et al. *Angewandte Chemie* 2014, 53(29): 7461-7465. The significant extension in the timeframe of insulin stability afforded by supramolecular PEGylation with PEG-T-CB [7] observed here is therefore noteworthy. Furthermore, this was achieved using a non-covalent supramolecular modification approach, demonstrating a viable alternative to methods that have stabilized insulin through covalent PEGylation on the B1 N-terminal amine. Previously published findings have suggested unmodified CB[7] can inhibit amyloid formation as measured by the ThT assay, whereas the studies performed here suggest covalent PEG conjugation to the CB[7] is required to inhibit aggregation of insulin upon supramolecular modification.

Figure 4A:
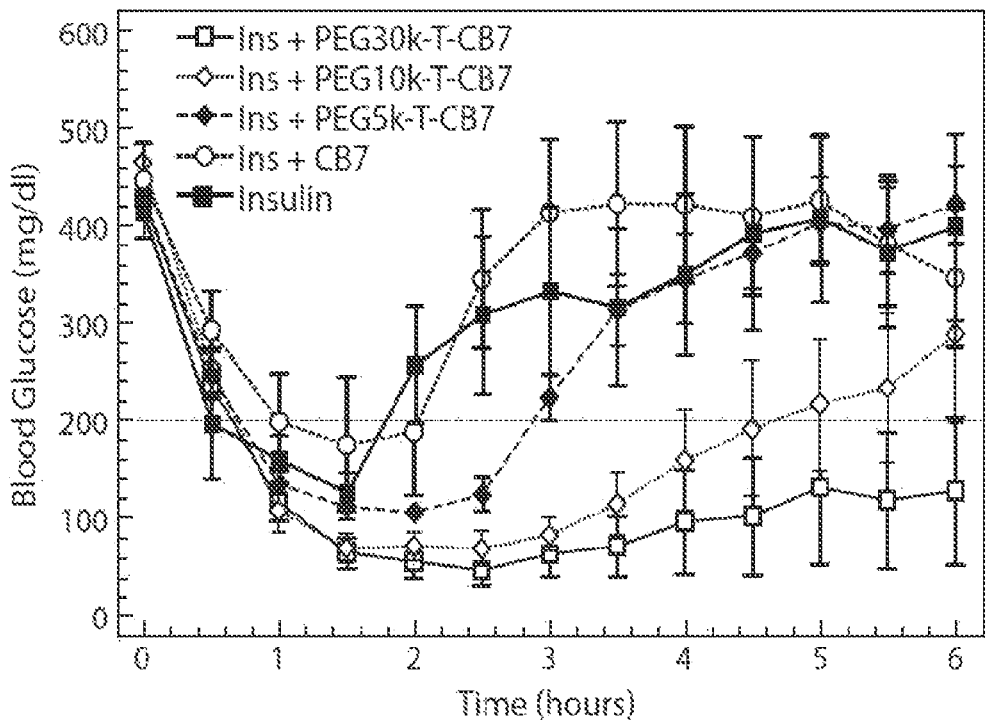
FIG. 4A. In vivo performance of CB[7] conjugates. In vivo assessment of blood glucose levels in STZ diabetic mice following administration of native insulin (1 IU/kg) injected alone or formulated with CB[7] or the PEG-T-CB [7] conjugates. Insulin was injected at t=0, and blood glucose was monitored for 6 hours following insulin administration (n=5 mice/group). The dotted gray line shows the standard criteria for normoglycemic in this strain of mice (<200 mg/dL).
Figure 4B:
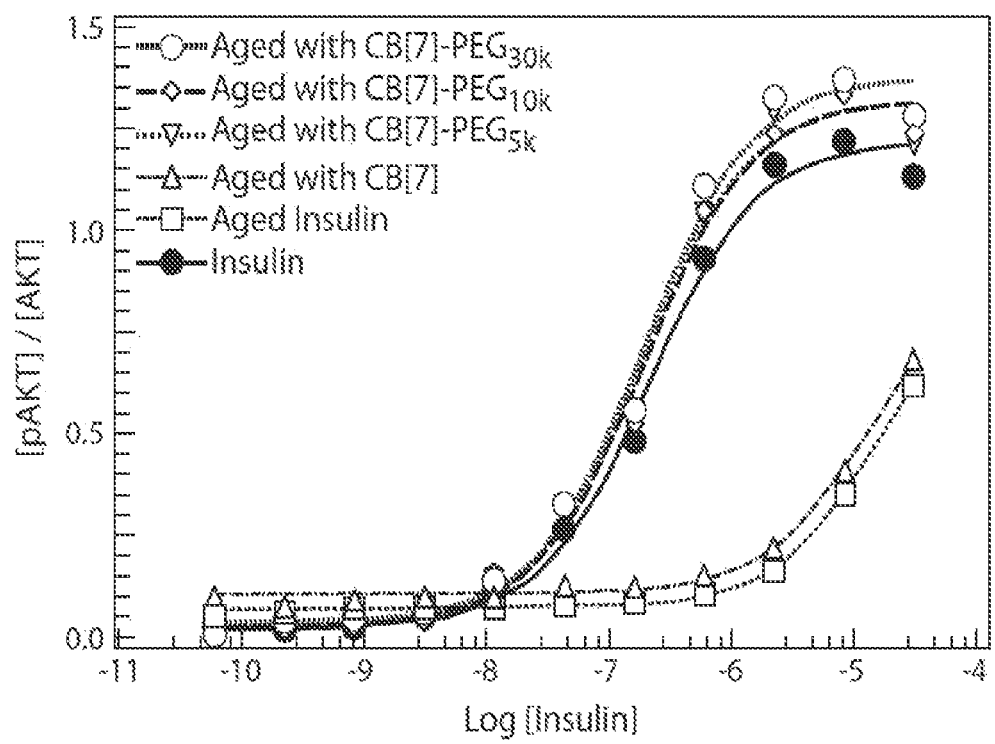
FIG. 4B. Insulin aged under physiologic conditions with continuous agitation for 100 days in formulation with CB[7]-PEG conjugates retains its activity when assaying for phosphorylation of Ser[473] on AKT (formulation potency: Aged Insulin, Log $EC_{50}$=−4.8±0.06; CB[7], Log $EC_{50}$=−4.9±0.07; CB[7]-$PEG_{5k}$, Log $EC_{50}$=−6.8±0.04; CB[7]-$PEG_{10k}$, Log $EC_{50}$=−6.7±0.04; CB[7]-$PEG_{30k}$, Log $EC_{50}$=−6.7±0.04 Fresh Insulin, Log $EC_{50}$=−6.8±0.04).
Figure 5:
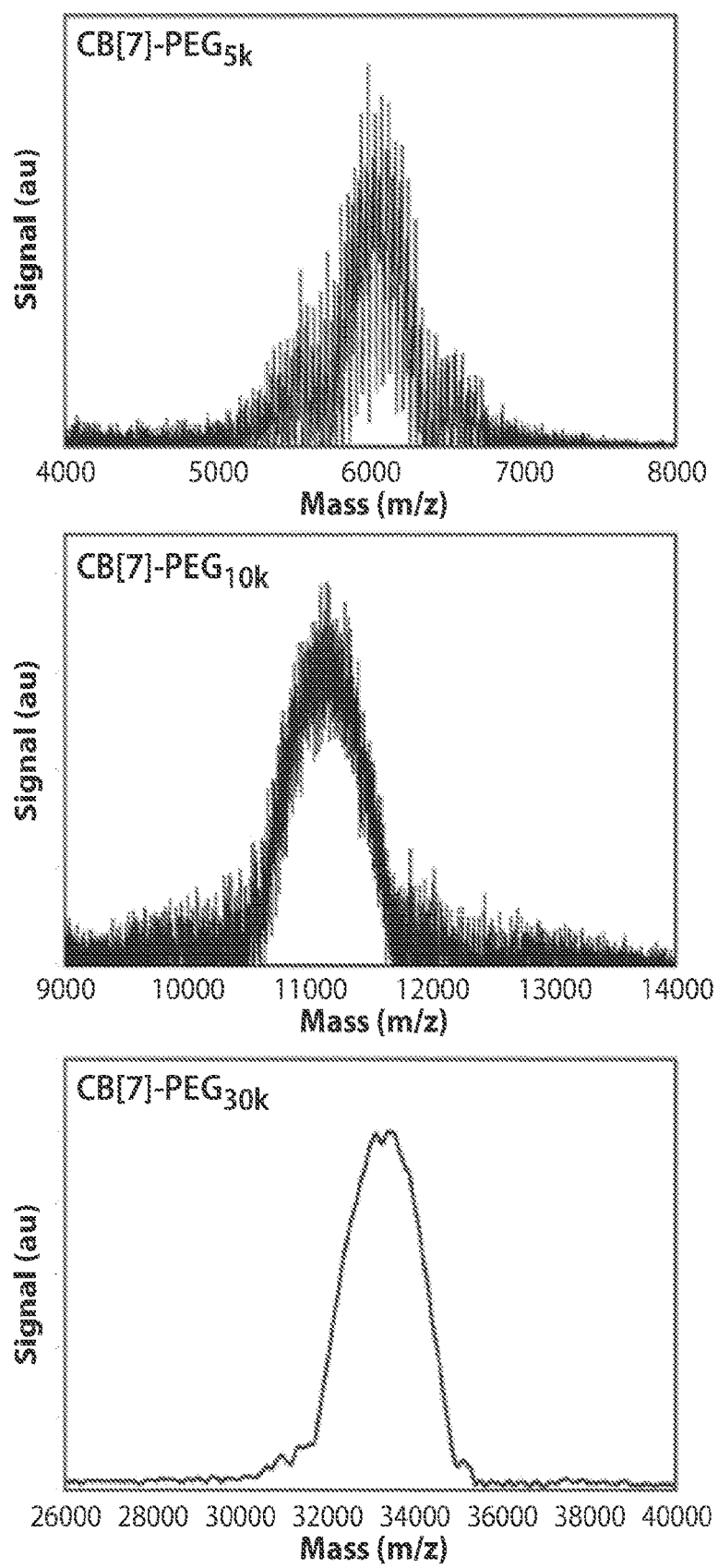
FIG. 5. Matrix assisted laser desorption ionization mass spectroscopy (MALDI-MS) of CB[7]-PEG conjugates following click-addition of CB[7]-$N_3$ to PEG-DBCO.
Figure 6:
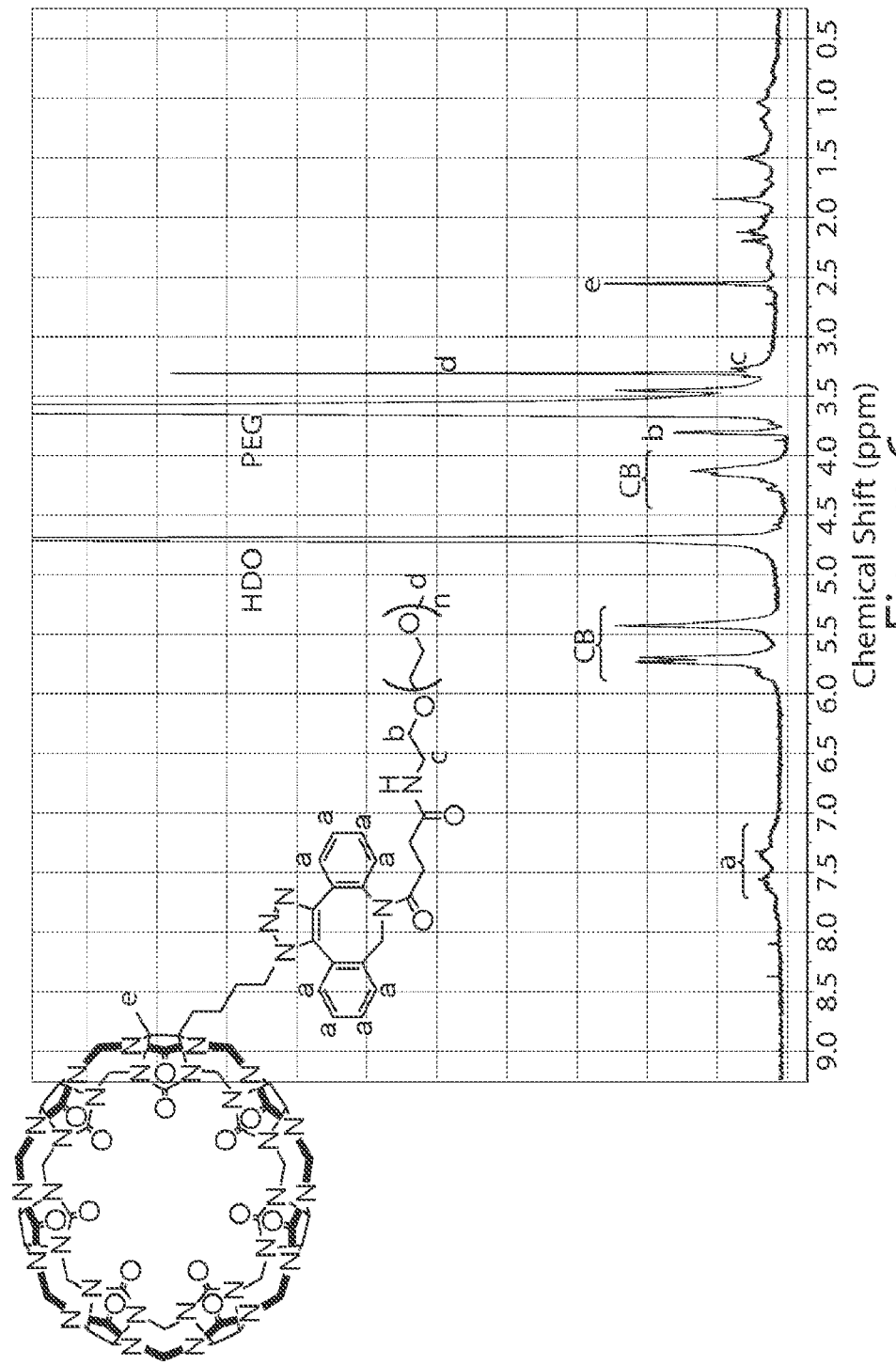
FIG. 6. $^1$H-NMR (400 MHz) of $PEG_{5k}$-T-CB[7] in $D_2O$.

A mouse model of insulin-deficient diabetes, prepared using streptozotocin to induce pancreatic ß-cell death, was used to evaluate the function of PEG-T-CB[7] conjugates in vivo (FIG. 4A). Following the onset of diabetes, mice were fasted overnight to ensure an average starting blood glucose level of approximately 450 mg/dL. See, e.g., Like et al. *Science* 1976, 193(4251): 415-417. Insulin was then administered subcutaneously at a dose of 1 IU/kg in a saline vehicle. Alternatively, an identical dose of insulin was administered along with CB [7], $PEG_{5k}$-T-CB[7], $PEG_{10k}$-T-CB [7], or $PEG_{30k}$-T-CB [7]. All insulin formulations reduced average blood glucose to a normoglycemic level (<200 mg/dL for a mouse) following a single subcutaneous administration. Animals that received either native insulin or insulin formulated with unmodified CB[7] became hyperglycemic again approximately 2 hours following administration. Animals that received insulin formulated with $PEG_{5k}$-T-CB[7] and $PEG_{10k}$-T-CB[7] remained normoglycemic for approximately 3 hours and 5 hours, respectively, following administration. Insulin formulated with $PEG_{30k}$-T-CB [7] preserved normoglycemia until the 6-hour endpoint of the study, at which time the average blood glucose level of mice in this group was 129 mg/dL, remaining well within the normoglycemic range. Thus, the duration of activity for native insulin is directly dependent on molecular weight of PEG in the PEG-T-CB[7] conjugate. Pharmacological function of the authentic native insulin protein can therefore be controlled by non-covalent modification, enabling the duration of therapy to be tuned through conjugate selection without a need for direct modification to the therapeutic protein.

The mechanism by which PEG-T-CB[7] extends the activity of insulin in vivo is likely multifactorial. First, insulin administered subcutaneously must reach vascular circulation prior to eliciting its function. Subcutaneous administration of compounds <1 kDa in molecular weight are typically preferentially absorbed directly via capillary circulation, while larger compounds (including insulin) primarily leverage fluid flux of lymphatic circulation to reach the vasculature, resulting in delayed systemic bioavailability. See, e.g., McLennan et al. *Drug discovery today Technologies* 2005, 2(1): 89-96; Swartz M A. *Adv Drug Deliv Rev* 2001, 50(1-2): 3-20; Chertok et al. *Mol Pharm* 2013, 10(10): 3531-3543. Moreover, it is known that molecular weight affects the rate at which compounds can traffic within lymphatic circulation. See, e.g., Supersaxo et al. *Pharmaceutical research* 1990, 7(2): 167-169. Therefore, supramolecular PEGylation of insulin with PEG chains of various molecular weights could contribute to delayed uptake and create a sustained depot of insulin in the subcutaneous space by increasing the effective molecular weight of the therapeutic protein. Once in circulation, native insulin is primarily cleared through internalization following binding to the insulin receptor. See, e.g., Di Guglielmo et al. *Molecular and cellular biochemistry* 1998, 182(1-2): 59-63. Covalent PEGylation of the B1 phenylalanine is known to induce a reduction in insulin bioactivity and reduced receptor activation. Therefore, supramolecular PEGylation could ensure insulin is cleared less quickly via receptor internalization by sequestering the insulin in a less active form for an extended time in circulation, whereby it would remain in equilibrium with the active free insulin species on account of the dynamic supramolecular interactions of CB[7] with insulin. Native insulin (5.8 kDa) is also subject to glomerular filtration, where it is subsequently degraded through enzymatic action. See, e.g., Rabkin et al. *Diabetologia* 1984, 27(3): 351-357. It is generally held that proteins or polymers (including PEG) greater than approximately 30 kDa in molecular weight are too large for significant uptake by the glomerulus. See, e.g., Caliceti et al. *Adv Drug Deliv Rev* 2003, 55(10): 1261-1277. Therefore, the supramolecular PEGylation of insulin with PEG-T-CB[7] could also reduce renal clearance, again by increasing the effective molecular weight of the protein. Additionally, PEGylation is well known to provide a steric protective effect on proteins in limiting access by proteolytic enzymes, a role that could also be filled by supramolecular PEGylation. It has previously been speculated that binding of CB[7] to the N-terminal phenylalanine is not likely to occur to any significant extent in circulation in vivo because the insulin concentration in normal serum is below the $K_D$ for binding of CB[7] to insulin; additionally, a high concentration of serum proteins that bind weakly to CB[7] could induce dissociation by competition. In light of this, the underlying mechanism is likely to favor a subcutaneous depot effect, whereby the PEG-T-CB[7] conjugates slow the absorption of insulin into the circulation and/or protect insulin from proteolysis when bound at high concentration in the depot relative to systemic concentrations upon uptake into the vasculature.

The PEG-T-CB[7] conjugates described here could be more broadly used to promote stability and increase the duration of action for a number of biopharmaceuticals. Insulin is an excellent candidate to demonstrate this approach, as it is a widely used biopharmaceutical, highly prone to amyloid formation, and possesses an N-terminal aromatic residue necessary for strong binding to CB[7]. See, e.g., Urbach et al. *Israel Journal of Chemistry* 2011, 51(5-6): 664-678. In fact, there is limited incidence of N-terminal aromatic residues in the human proteome, meaning most biopharmaceuticals would not have native sequences amenable to binding with CB [7]. However, the installation of a phenylalanine or tryptophan residue, or perhaps even a non-canonical amino acid capable of binding to CB[7], onto the N-terminus of many therapeutic proteins could improve compatibility with the supramolecular PEGylation strategy outlined here. See, e.g., Logsdon et al. *Journal of the American Chemical Society* 2011, 133(42): 17087-17092. As described herein, this is an attractive and useful strategy for modifying any protein.

PEGylation of Glucagon and Anti-CD20 Antibody

Glucagon and an antibody for human CD20—a variant of which is used clinically as Rituximab—were also evaluated for stability when formulated with CB[7]-PEG. Even in the absence of an N-terminal aromatic, lower affinity interactions between CB[7] and mid-chain residues were sufficient to confer improved stability. Anti-CD20, when agitated in the presence of CB[7]-PEG, maintained activity toward a B-cell lymphoma cell line (FIG. 9A). Glucagon, which typically has aqueous solubility of less than one hour, remained soluble and in its active α-helical conformation for at least 24 hours when formulated with CB[7]-PEG (FIGS. 9B and 9C).

Methods

Synthesis of CB[7]-PEG Conjugates

Dibenzocyclooctyne-functional poly(ethylene glycol) (PEG-DBCO) with approximate molecular weights of 5 kDa, 10 kDa, and 30 kDa were purchased from Click Chemistry Tools, LLC, whereas monofuntional CB[7]-$N_3$ was synthesized as described previously. See, e.g., Vinciguerra et al. *Journal of the American Chemical Society* 2012, 134(31): 13133-13140. Commercially sourced PEG-DBCO derivatives (100 mg, 1.05 equivalent) were mixed with CB[7]-$N_3$ (1 equivalent) in $H_2O$/DMSO (4 ml, 1:1 v/v) and stirred at 60° C. for 24 hours. The reaction mixture was lyophilized and the product was characterized by MALDI-MS (FIGS. 2A-2D and FIG. 5) and $^1$H-NMR (400 MHz; FIG. 6). Gel permeation chromatography (GPC) was performed in water on a glucose-modified divinylbenzene column utilizing a Malvern Viscotek™ system with both refractive index and UV-visible detectors at a 1.0 mL/min flow rate. Samples were filtered through 0.2 μm PVDF filters prior to injection onto the column.

Acridine Orange Competitive Binding Assay

Binding of PEG-T-CB[7] conjugates to insulin was assessed using the acridine orange dye displacement assay, in accordance with a previously described protocol. See, e.g., Chinai et al. *Journal of the American Chemical Society* 2011, 133(23): 8810-8813 Briefly, 6 μM of either unmodified CB[7] or the PEG-T-CB[7] conjugates and 8 μM acridine orange were combined with recombinant insulin (0, 1, 2, 4, 6, 8, 10, 12.5, 15 μM) in $H_2O$. Samples were incubated overnight in light-free conditions and fluorescent spectra were collected on an Infinite® M1000 plate reader (Tecan Group, Ltd.), exciting at 485 nm and collecting the resulting fluorescent spectra from 495-650 nm. The decay in the peak of acridine orange fluorescent signal was fit to a one-site competitive binding model (GraphPad Prism v6.0), using the CB[7]•AO equilibrium constant reported previously ($K_{eq}=2\times10^5$ $M^{-1}$), to determine binding constants of unmodified CB[7] and PEG-T-CB[7] to native insulin. See, e.g., Shaikh et al. *Photochemical & photobiological sciences: Official journal of the European Photochemistry Association and the European Society for Photobiology* 2008, 7(4): 408-414.

Circular Dichroism

Recombinant human insulin was dissolved at 0.25 mg/ml in $H_2O$ in combination with 1 equivalent of PEG-T-CB[7] and samples were left to equilibrate for 3 hours at room temperature. Near-ultraviolet circular dichroism spectroscopy was performed with a Jasco J-1500 high performance circular dichroism spectrometer over a wavelength range of 190-250 nm using a 0.1 cm path-length cell.

Insulin Aggregation Assay

Recombinant human insulin was dissolved at 4 mg/ml in 2 mM HCl with 150 mM NaCl. Insulin was diluted to a final concentration of 1 mg/ml in phosphate buffered saline in combination with 1 equivalent of unmodified CB[7] or PEG-T-CB[7] conjugates. Samples were plated 150 μl per well (n=4/group) in an clear 96-well plate (Thermo Scientific Nunc) and sealed with optically clear and thermally stable seal (VWR). The plate was immediately placed into an Infinite® M1000 plate reader (Tecan Group, Ltd.) and shaken continuously at 37° C. Absorbance readings at 540 nm were collected every 6 minutes for 100 hours, and absorbance values were subsequently converted to transmittance. The aggregation of insulin leads to light scattering, which results in reduction of sample transmittance. The time for aggregation ($t_A$) was defined as a >10% reduction in transmittance from the initial transmittance. Following the 100-hour kinetic study, the plate was maintained under continuous agitation at 37° C. and absorbance at 540 nm was monitored daily to approximate $t_4$ for the PEG-T-CB[7] conjugates.

In Vitro Insulin Activity

C2C12 cells were purchased from the American Type Culture Collection (ATCC) and confirmed free of *mycoplasma* contamination prior to use. Cells were cultured in Dulbecco's modified Eagle medium (DMEM) containing L-glutamine, 4.5 g/L D-glucose, and 110 mg/L sodium pyruvate, and supplemented with 10% fetal bovine serum and 1% penicillin-streptomycin. Incubations occurred in a 5% $CO_2$/water-saturated incubator at 37° C. Cells were seeded in 96-well plates at a density of 5,000 cells per well. Twenty-four hours after plating, the cells were washed twice with 200 μL of DMEM containing L-glutamine, 4.5 g/L glucose, and 110 mg/L sodium pyruvate, and starved for 2 hours at 37° C. in the same serum-free conditions. After 2 hours the media was removed and cells were stimulated with 100 μL of insulin samples of various concentrations for 30 minutes at 37° C. After 30 minutes, cells were washed twice with 100 μL of cold Tris-buffered saline (1×), followed by lysing the cells for 10 minutes with 100 μL of cold Lysis Buffer (Perkin Elmer). Levels of phosphorylated AKT 1/2/3 (Ser473) and total AKT 1 were determined from cell lysates using the AlphaLISA® SureFire® ULTRA™ kits (Perkin Elmer) according to the manufacturer's instructions. Intra-well normalized data of phosphorylated AKT 1/2/3 (Ser473) and total AKT 1 were analyzed using Graph Pad Prism 6.0, with dose-response curves fitted to a variable slope (three parameter) stimulation model to determine the $EC_{50}$ of each insulin sample.

In Vivo Assessment of Performance

Male C57BL/6J, age 8 weeks, were purchased the Jackson Laboratory. Upon acclimation for one week in the animal facility, mice were fasted for 4 hours prior to intraperitoneal injection of 150 mg/kg streptozotocin (STZ, Sigma). STZ for injection was dissolved at a concentration of 22.5 mg/ml in 2.94% (w/v) in pH 4.5 sodium citrate buffer immediately prior to injection. Mice were allowed to eat ad libitum and glucose levels were monitored by peripheral tail vein bleeds using a portable glucose meter (Accu-Chek Aviva, Roche) daily until unfasted glucose levels >400 mg/dL. STZ-induced diabetic mice were fasted overnight prior to assessing insulin performance. Mice were bled at the beginning of the study, and any mouse with a fasting blood glucose level below 300 mg/dL was triaged from the study. Mice were then randomized and injected subcutaneously with insulin dosed at 1 IU/kg (34.7 μg/kg) either alone or formulated with 5 molar equivalents of unmodified CB[7] or PEG-T-CB[7] conjugates. In all case, insulin with and without CB[7] or PEG-T-CB[7] was injected in a 200 μL saline vehicle. Blood glucose readings were collected every 30 minutes using a handheld glucose meter for 6 hours following insulin injection.

Antibody Stability Assessment

Mouse anti-human CD20 IgG (Biolegend) was dissolved at 0.5 mg/ml in PBS alone, or with 2 equivalents of CB[7] or CB[7]-PEG conjugates for a total volume of 200 μl into 2 ml glass vials. Into each vial, five 1 mm polystyrene beads (Sigma) were added. The samples were subject to vortex agitation continuously for 24 hours to induce aggregation. As a CD20-positive cell source, human Raji B-cell lymphoma cells (ATCC) were grown in RPMI 1640 media supplemented with 10% fetal bovine serum and passaged four times prior to experiments. For each antibody sample, one million cells were mixed in 100 μl of various antibody formulations, diluted to a concentration of 1 μg/ml based on a dilution for this antibody determined in separate controls to be an appropriate dilution below saturation for these specific cells. Cells were incubated with anti-CD20 antibody (100 μl at 1 μg/ml) for 25 minutes, following which they were washed, combined with a secondary goat-anti-mouse IgG labeled with Alexa Fluor® 555 (1:500 dilution, Biolegend) and incubated for 25 minutes. Following additional washes, cells were suspended in 500 μl buffer and analyzed on an LSRFortessa (BD Biosciences) flow cytometer. Data was analyzed by FlowJo v10.1.

Glucagon Stability Assessment

Human recombinant glucagon (Sigma) was dissolved at 4 mg/ml in PBS containing 1 mM HCl. This was mixed 1:1 with 1 equivalent of CB[7]-$PEG_{10k}$ in PBS, or in PBS alone, for a final glucagon concentration of 2 mg/ml. Vials were left to age at room temperature for various times. Circular dichroism was performed on samples without dilution, as well as on freshly dissolved glucagon, by utilizing a 100 am-pathlength cuvette.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. An agent associated with a tag, wherein:
   the agent is directly bound to a macrocyclic host via non-covalent interactions; and
   the macrocyclic host is conjugated to the tag; wherein
   the agent is a protein or peptide;
   the tag is a polymer; and
   the macrocyclic host is an optionally substituted cucurbit[7]uril (CB[7]).

2. The agent of claim 1, wherein the agent is a protein.

3. The agent of claim 2, wherein the protein is an antibody.

4. The agent of claim 1, wherein the macrocyclic host is conjugated to the tag via a linker.

5. The agent of claim 4, wherein the linker is of Formula (L-1):

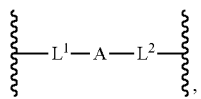

(L-1)

wherein:
each of $L^1$ and $L^2$ is independently a bond, optionally substituted alkylene, or optionally substituted heteroalkylene; and
A is a bond, optionally substituted heterocyclyl, or optionally substituted heteroaryl.

6. The agent of claim 1, wherein the non-covalent interactions are guest-host interactions.

7. The agent of claim 1, wherein the agent is a protein, and the macrocyclic host binds an amino acid residue of the protein.

8. The agent of claim 7, wherein the macrocyclic host binds an amino acid selected from the group consisting of phenylalanine, tryptophan, and tyrosine.

9. A compound comprising an optionally substituted cucurbituril cucurbit[7]uril (CB [7]) conjugated to a tag, or a salt thereof; wherein the tag is a polymer.

10. The compound of claim 9, wherein the compound is of Formula (CB-1):

(CB-1),
or a salt thereof, wherein:
CB is an optionally substituted CB [7];
TAG is a polymer;
each of $L^1$ and $L^2$ is independently a bond, optionally substituted alkylene, or optionally substituted heteroalkylene; and
A is a bond, optionally substituted heterocyclyl, or optionally substituted heteroaryl.

11. A compound of Formula (CB-2a) or Formula (CB-2b):

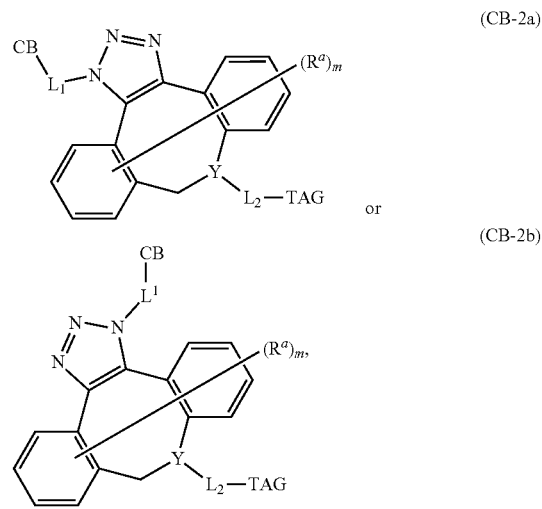

or a salt thereof, wherein:
CB is an optionally substituted cucurbituril;
TAG is a tag selected from the group consisting of polymers, therapeutic agents, targeting agents, radionuclides, fluorophores, chromophores, phosphorescent agents, dyes, chemiluminescent agents, particles, colorimetric labels, magnetic labels, haptens, biomolecules, small molecules, fatty acids, hydrocarbon chains, excipients, and diagnostic agents;
each of $L^1$ and $L^2$ is independently a bond, optionally substituted alkylene, or optionally substituted heteroalkylene;
Y is $CR^a$ or N;
each instance of Ra is independently hydrogen, halogen, optionally substituted alkyl, optionally substituted heteroalkyl, optionally substituted alkenyl, optionally substituted alkynyl, optionally substituted acyl, optionally substituted carbocyclyl, optionally substituted heterocyclyl, optionally substituted aryl, optionally substituted heteroaryl, optionally substituted acyl, $-OR^{aa}$, $-SR^{aa}$, $-N(R^{aa})_2$, $-NO_2$, or $-CN$, or two $R^a$ attached to adjacent atoms are joined to form an optionally substituted carbocyclyl, optionally substituted heterocyclyl, optionally substituted aryl, or optionally substituted heteroaryl ring;
each occurrence of $R^{aa}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group when attached to an oxygen atom, or a nitrogen protecting group when attached to a nitrogen atom, or two $R^{aa}$ attached to the same nitrogen atom are joined to form an optionally substituted heterocyclic or optionally substituted heteroaryl ring; and m is 0 or an integer from 1-10, inclusive.

12. The compound of claim 11, wherein the compound is of Formula (PEG-T-CB[7]):

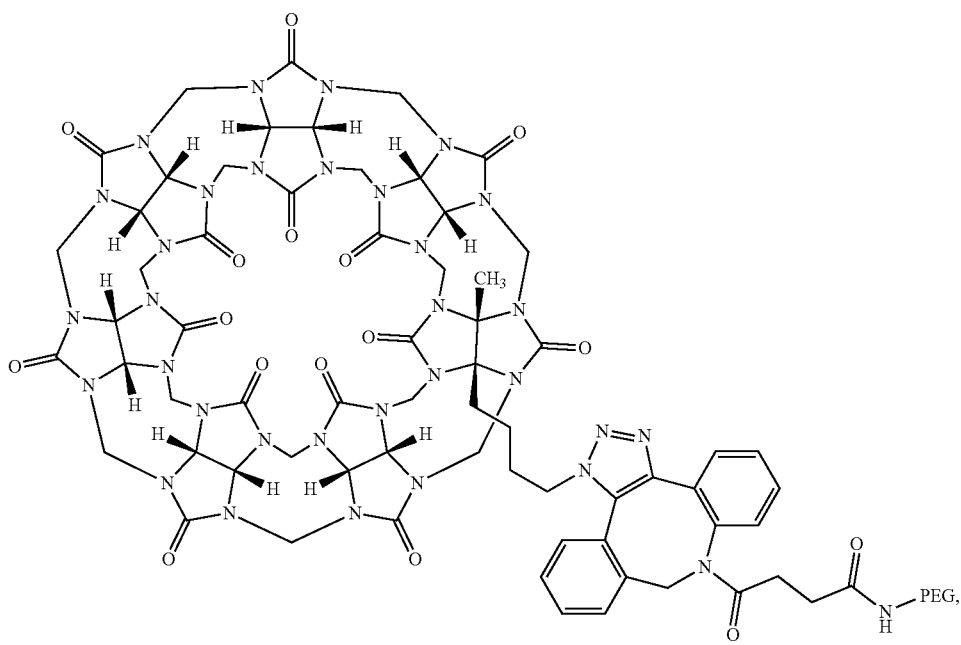

(PEG-T-CB[7])

or a salt thereof.

13. A pharmaceutical composition comprising an agent of claim 1, and a pharmaceutically acceptable excipient.

14. The agent of claim 2, wherein the protein is a therapeutic protein.

15. The agent of claim 2, wherein the protein is unmodified.

16. The agent of claim 2, wherein the protein is insulin.

17. The agent of claim 2, wherein the protein is glucagon.

18. The agent of claim 1, wherein the polymer is a polyether, polyboronic acid, or polyboronic ester.

19. The agent of claim 1, wherein the polymer is polyethylene glycol (PEG).

20. The agent of claim 1, wherein the agent is insulin; and the tag is polyethylene glycol (PEG).

21. The agent of claim 1, wherein the agent is glucagon; and the tag is polyethylene glycol (PEG).

22. The agent of claim 1, wherein the agent is glucagon; and the tag is a polyboronic acid or polyboronic ester.

23. The agent of claim 1, wherein the agent is an antibody; and the tag is polyethylene glycol (PEG).

24. The compound of claim 9, wherein the polymer is a polyether, polyboronic acid, or polyboronic ester.

25. The compound of claim 9, wherein the polymer is polyethylene glycol (PEG).

26. The compound of claim 11, wherein CB is optionally substituted CB[7].

27. The compound of claim 11, wherein TAG is a polymer.

28. The compound of claim 27, wherein the polymer is a polyether, polyboronic acid, or polyboronic ester.

29. The compound of claim 28, wherein the polymer is polyethylene glycol (PEG).

30. The compound of claim 11, wherein the compound is of Formula (CB-3a) or (CB-3b):

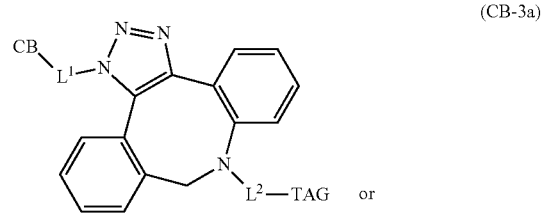

(CB-3a)

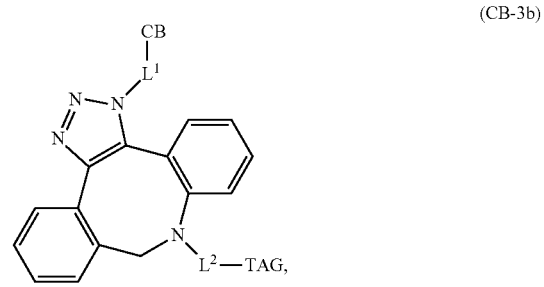

(CB-3b)

or a pharmaceutically acceptable salt thereof.

* * * * *